(12) United States Patent
Snyder et al.

(10) Patent No.: US 9,937,144 B2
(45) Date of Patent: Apr. 10, 2018

(54) TREATMENT OF DRUG ABUSE BY PREVENTING GAPDH NITROSYLATION

(71) Applicant: THE JOHNS HOPKINS UNIVERSITY, Baltimore, MD (US)

(72) Inventors: Solomon H. Snyder, Baltimore, MD (US); Nilkantha Sen, Augusta, GA (US); Risheng Xu, Baltimore, MD (US)

(73) Assignee: THE JOHNS HOPKINS UNIVERSITY, Balitimore, MD (US)

( * ) Notice: Subject to any disclaimer, the term of this patent is extended or adjusted under 35 U.S.C. 154(b) by 0 days.

(21) Appl. No.: 14/763,956

(22) PCT Filed: Jan. 30, 2014

(86) PCT No.: PCT/US2014/013775
§ 371 (c)(1),
(2) Date: Jul. 28, 2015

(87) PCT Pub. No.: WO2014/120885
PCT Pub. Date: Aug. 7, 2014

(65) Prior Publication Data
US 2015/0359776 A1 Dec. 17, 2015

Related U.S. Application Data

(60) Provisional application No. 61/758,461, filed on Jan. 30, 2013.

(51) Int. Cl.
A61K 31/335 (2006.01)
A61K 31/137 (2006.01)
G01N 33/573 (2006.01)

(52) U.S. Cl.
CPC .......... *A61K 31/335* (2013.01); *A61K 31/137* (2013.01); *G01N 33/573* (2013.01); *G01N 2333/90203* (2013.01); *G01N 2500/02* (2013.01)

(58) Field of Classification Search
None
See application file for complete search history.

(56) References Cited

U.S. PATENT DOCUMENTS

| | | |
|---|---|---|
| 5,444,095 A | 8/1995 | Tatton et al. |
| 6,299,901 B1 | 10/2001 | DiSanto et al. |
| 6,313,176 B1 | 11/2001 | Ellinwood, Jr. et al. |
| 6,635,667 B2 | 10/2003 | Thomas |
| 6,806,057 B2 | 10/2004 | Snyder et al. |
| 7,001,738 B2 | 2/2006 | Snyder et al. |
| 7,875,648 B2 | 1/2011 | Meier |
| 2002/0132829 A1 | 9/2002 | Tatton et al. |
| 2002/0155172 A1 | 10/2002 | Yuan et al. |
| 2004/0063612 A1 | 4/2004 | Yalpani |
| 2005/0026227 A1 | 2/2005 | Snyder et al. |
| 2005/0222269 A1 | 10/2005 | Tatton et al. |
| 2007/0293505 A1 | 12/2007 | McCreary et al. |
| 2010/0022659 A1 | 1/2010 | Meyerson et al. |

FOREIGN PATENT DOCUMENTS

| | | | |
|---|---|---|---|
| EP | 0726265 A1 | 7/2001 | |
| WO | 1992/021333 A2 | 12/1992 | |
| WO | 1997/45422 A1 | 12/1997 | |
| WO | 2004/066993 A1 | 8/2004 | |
| WO | 2005/044255 A1 | 5/2005 | |
| WO | WO 2005/044255 * | 5/2005 | ........... A61K 31/335 |
| WO | 2005/072705 A1 | 8/2005 | |

OTHER PUBLICATIONS

Dagher et al (Neuron 61:502-510, 2009).*
Hara, M., et al., "Neuroprotection by pharmacologic blockade of the GAPDH death cascade", PNAS, (2006) vol. 103, No. 10, pp. 3887-3889.
Hara, M., et al., "Nitric oxide-GAPDH-Siah: a novel cell death cascade", Cellular and Molecular Neurobiology, (2006) vol. 26, Nos. 4-6, pp. 527-538.
Sen, N., et al., "Gospel: a neuroprotective protein that binds to GAPDH upon S-nitrosylation", Neuron, (2009), vol. 63, pp. 81-91.
Kragten, E. et al., "Glyceraldehyde-3-phosphate dehydrogenase, the putative target of the antiapoptotic compounds CGP 3466 and R-(-)-deprenyl" J Biol Chem. Mar. 6, 1998; vol. 273, No. 10, pp. 5821-5828.
Itzhak, Y., et al., "The role of neuronal nitric oxide synthase in cocaine-induced conditioned place preference" Neuroreport. Aug. 3, 1998, vol. 9, No. 11, pp. 2485-2488.
Nasif, F., et al., "Inhibition of neuronal nitric oxide synthase prevents alterations in medial prefrontal cortex excitability induced by repeated cocaine administration" Psychopharmacology (Berl) (2011) vol. 218, No. 2, pp. 323-330.
Balda, M., et al., "Differential role of the nNOS gene in the development of behavioral sensitization to cocaine in adolescent and adult B6;129S mice", Psychopharmacology (Berl). Nov. 2008;200(4):509-19.

(Continued)

*Primary Examiner* — Craig D Ricci
(74) *Attorney, Agent, or Firm* — Johns Hopkins Technology Ventures

(57) ABSTRACT

The present invention relates to the field of drug abuse. More specifically, the present invention provides methods and compositions for treating drug abuse by preventing GAPDH nitrosylation. In one specific embodiment, a method for preventing the stimulant and neurotoxic effects of cocaine comprises the step of administering a compound that prevents the nitrosylation of glyceraldehyde-3-phosphate dehydrogenase (GAPDH) by nitric oxide (NO). In another embodiment, a method for preventing the stimulant and neurotoxic effects of cocaine comprises the step of administering a compound that prevents the binding of GAPDH to Siah.

3 Claims, 28 Drawing Sheets

(56) References Cited

OTHER PUBLICATIONS

Sen. N., et al. "Nitric oxide-induced nuclear GAPDH activates p300/CBP and mediates apoptosis" Nat Cell Biol. Jul. 2008;10(7):866-73.

Fumagalli, F., et al., "Single session of cocaine intravenous self-administration shapes goal-oriented behaviours and up-regulates Arc mRNA levels in rat medial prefrontal cortex" Int J Neuropsychopharmacol Apr. 2009;12(3):423-9.

Kuzmin, A., et al. "Expression of c-fos, NGFI-A and secretogranin II mRNA in brain regions during initiation of cocaine self-administration in mice" Eur J Neurosci. Oct. 1999;11(10):3694-700.

Ho M., et al., "Chronic treatment with monoamine oxidase-B inhibitors decreases cocaine reward in mice" Psychopharmacology (Berl). Jul. 2009;205(1):141-9.

Gatch, M., et al., Effects of monoamine oxidase inhibitors on cocaine discrimination in rats. Behav Pharmacol. Mar. 2006;17(2):151-9.

Hara, M., et al., "Neuroprotection by pharmacologic blockade of the GAPDH death cascade" PNAS, Mar. 7, 2006, vol. 103, No. 10, pp. 3887-3889.

Graham, D., et al., "Dynamic BDNF activity in nucleus accumbens with cocaine use increases self-administration and relapse", Nature Neuroscience vol. 10, No. 8, Aug. 2007.

Im, H., et al., "MeCP2 controls BDNF expression and cocaine intake through homeostatic interactions with microRNA-212", Nature Neuroscience vol. 13, No. 9, Sep. 2010.

Larson, E., et al., "Striatal regulation of FosB, FosB, and cFos during cocaine self-administration and withdrawal", Journal of Neurochemistry (2010) vol. 115, pp. 112-122.

Maza, I., et al. "Essential role of the histone methyltransferase G9a in cocaine-induced plasticity" Science. Jan. 8, 2010;327(5962):213-6.

McClung, C., et al., "Regulation of gene expression and cocaine reward by CREB and ΔFosB", Nature Neuroscience vol. 6, No. 11, Nov. 2003.

McGinty, J., et al., "Brain-derived neurotrophic factor and cocaine addiction", Brain Research (2010), 1314, pp. 183-193.

Noda, Y., et al., "Involvement of Signal Transduction Cascade via Dopamine-D1 Receptors in Phencyclidine Dependence", Annals New York Academy of Science, 1025: 62-68 (2004).

Robison, A., et al., "Transcriptional and epigenetic mechanisms of addiction", Nature Reviews Neuroscience Nov. 2011, vol. 12, pp. 623-637.

Sagot, Y., et al., "An orally active anti-apoptotic molecule (CGP 3466B) preserves mitochondria and enhances survival in an animal model of motoneuron disease", Br J Pharmacol. Oct. 2000;131(4):721-8.

Sen, N., et al., Neurotrophin-mediated degradation of histone methyltransferase by S-nitrosylation cascade regulates neuronal differentiation. Proc Natl Acad Sci U S A. Dec. 13, 2011;108(50):20178-83.

Taniguchi, M., et al., "Histone Deacetylase 5 Limits Cocaine Reward through cAMP-Induced Nuclear Import", Neuron 73, 108-120, Jan. 12, 2012.

Shoulson, et al., "Deprenyl and disability in early parkinson's disease", The Parkinson Study Group, The New England Journal of Medicine, Nov. 16, 1989, vol. 321, No. 20, pp. 1364-1371.

Thomas, M., et al., "Neuroplasticity in the mesolimbic dopamine system and cocaine addiction", British Journal of Pharmacology (2008) 154, 327-342.

Zhou, L., et al., "Neuronal nitric oxide synthase: Structure, subcellular localization, regulation, and clinical implications", Nitric Oxide 20 (2009) 223-230.

Lee, DK., et al., "Interactions of D1 and N-methyl-D-Aspartate Receptors are Required for Acute Cocaine-Evoked Nitric Oxide Efflux in the Dorsal Striatum", Exp Neurobiol. Jun. 2011;20(2):116-22.

Yasar, S., et al., "Evaluation of deprenyl for cocaine-like discriminative stimulus effects in rats", Eur J Pharmacol. Jul. 11, 1994;259(3):243-50.

Wu, W., et al., "The amphetamine-like reinforcing effect and mechanism of L-deprenyl on conditioned placepreference in mice", Eur J Pharmacol. Jan. 1, 1999;364(1):1-6.

Waldmeier, P., et al., "Neurorescuing effects of the GAPDH ligand CGP 3466B", J Neural Transm Suppl. 2000; (60):197-214.

\* cited by examiner

A

CGP 3466B

B

C

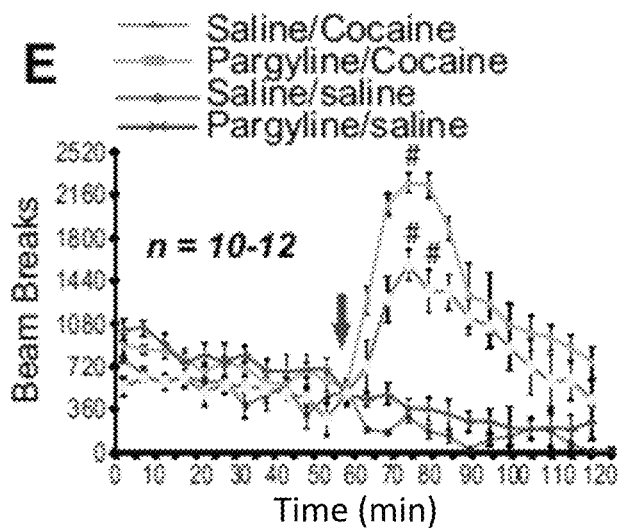
FIG. 4E
FIG. 4F
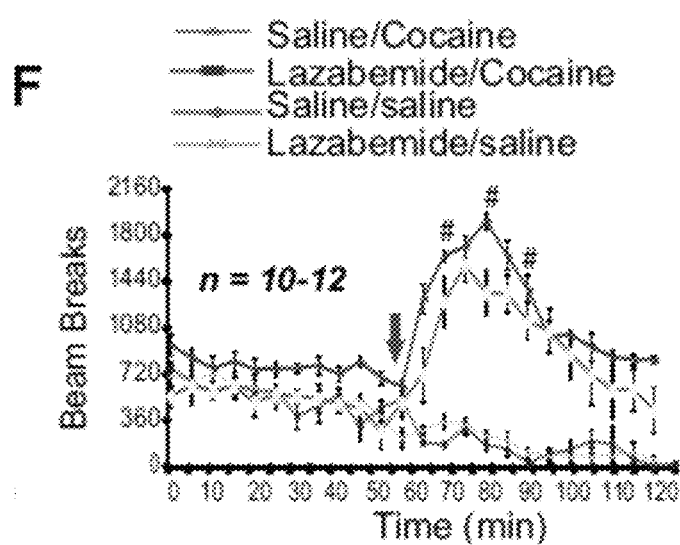

A

B

A

B

C

US 9,937,144 B2

TREATMENT OF DRUG ABUSE BY PREVENTING GAPDH NITROSYLATION

CROSS-REFERENCE TO RELATED APPLICATIONS

This application is a 35 U.S.C. § 371 U.S. national entry of International Application PCT/US2014/013775, having an international filing date of Jan. 30, 2014, which claims the benefit of U.S. Provisional Application No. 61/758,461, filed Jan. 30, 2013, the content of each of the aforementioned applications is herein incorporated by reference in their entirety.

STATEMENT OF GOVERNMENTAL INTEREST

This invention was made with government support under grant no. DA000266 awarded by the National Institutes of Health. The government has certain rights in the invention.

FIELD OF THE INVENTION

The present invention relates to the field of drug abuse. More specifically, the present invention provides methods and compositions for treating drug abuse by preventing GAPDH nitrosylation.

BACKGROUND OF THE INVENTION

The prevalence of drug use and abuse worldwide has reached epidemic levels. There are a plethora of drugs, both legal and illegal, the abuse of which have become serious public policy issues affecting all strata of society with medical and social consequences. Some users live in an extremely high risk population associated with poverty and illegal activity. Other users who might classify themselves as recreational users are at risk due to (a) properties of the drug(s) which make them addictive, (b) a predisposition of the user to become a heavy user or (c) a combination of factors including personal circumstances, hardship, environment and accessibility. Adequate treatment of drug abuse requires innovative and creative programs of intervention.

SUMMARY OF THE INVENTION

The present invention is based, at least in part, on the discovery that drugs which potently and selectively block nitrosylation of GAPDH, such as Deprenyl and CBP3466B, block both behavioral stimulant and neurotoxic pathways to prevent stimulant and neurotoxic actions of cocaine. Behavioral stimulant effects of cocaine are thought to be initiated by potentiation of the synaptic actions of dopamine and, possibly, serotonin associated with inhibition of neurotransmitter transport (1-3). Nuclear events triggered by cocaine, including chromatin remodeling (4-6), have been linked to behavioral actions with reports of increased signaling via transcription factors such as CREB and ΔfosB (7,8) leading to augmented expression of transcriptional targets such as BDNF 9-11 and immediate early genes such as c-fos, Arc (12). Mechanisms connecting neurotransmitter-receptor interactions to these transcriptional systems upon cocaine treatment have not been well characterized. The present inventors report that a signaling cascade involving nitric oxide (NO) and glyceraldehyde-3-phosphate dehydrogenase (GAPDH) mediates cocaine's transcriptional and behavioral actions. Lower, behavioral stimulant doses enhance the CREB signaling system, while higher, neurotoxic doses stimulate the p53 cytotoxic system. The drug CGP3466B, which potently and selectively blocks GAPDH nitrosylation and GAPDH-Siah binding, prevents these actions as well as behavioral effects of cocaine providing a novel strategy for anti-cocaine therapy.

Accordingly, in one aspect, the present invention provides methods for preventing the stimulant and neurotoxic effects of drugs. In certain embodiments, the methods are directed to preventing the stimulant and neurotoxic effects of cocaine. In one specific embodiment, a method for preventing the stimulant and neurotoxic effects of cocaine comprises the step of administering a compound that prevents the nitrosylation of glyceraldehyde-3-phosphate dehydrogenase (GAPDH) by nitric oxide (NO). In another embodiment, a method for preventing the stimulant and neurotoxic effects of cocaine comprises the step of administering a compound that prevents the binding of GAPDH to Siah. In a specific embodiment, the compound is CGP3446B. In another embodiment, the compound is Deprenyl.

In a further embodiment, a method for treating a cocaine user comprises the step of administering CGP3446B or Deprenyl in an amount sufficient to (1) prevent the nitrosylation of GAPDH by nitric oxide, (2) inhibit the binding of GAPDH to Siah, and/or (3) prevent the nuclear translocation of GAPDH. In a further embodiment, a method for treating a cocaine user comprises the step of administering a compound that prevents the nitrosylation of GAPDH by nitric oxide, (2) inhibits the binding of GAPDH to Siah, and/or (3) prevents the nuclear translocation of GAPDH. In certain embodiments, the compound is CGP3446B. In other embodiments, the compound is Deprenyl.

In another aspect, the present invention provides methods for identifying compounds. In one embodiment, a method for identifying compounds which interfere with the binding of GAPDH to Siah, the compounds being candidate therapeutic agents, comprises the steps of (a) contacting a first protein, a second protein and a test compound under conditions in which the first and second proteins bind to each other in the absence of the test compound, wherein the first protein comprises GAPDH and the second protein comprises Siah or the first protein comprises Siah and the second protein comprises GAPDH; (b) determining the quantity of the first protein which is bound to, is displaced from, or is prevented from binding to, the second protein; and (c) identifying as a candidate therapeutic agents a compound which diminishes the quantity of the first protein bound to the second protein, or which displaces first protein bound to the second protein, or which prevents first protein form binding to the second protein.

In a specific embodiment, an antibody is used to determine the quantity of the first protein which is bound to, is displaced from, or is prevented from binding to, the second protein. In another embodiment, one of the two proteins is fixed to a solid support. In yet another embodiment, one of the two proteins is labeled. In an alternative embodiment, an antibody specifically immunoreactive with the second protein is used to separate bound first protein from unbound first protein. In a further embodiment, at least one of the first and the second proteins is a fusion protein.

BRIEF DESCRIPTION OF THE FIGURES

FIGS. 1E and 1F: Quantitative ChIP analysis of binding of CREB and p53 to c-fos and PUMA promoters in striatum following cocaine treatment. Data were normalized by total input and presented as bound/input. *p<0.01, n=3, one-way ANOVA, mean±SEM. See also FIG. 6.

FIG. 2. Effect of GAPDH or C150S GAPDH on Behavioral and Neurotoxic Actions of Cocaine.

FIG. 3. CGP3466B Prevents Behavioral Actions of Cocaine.

FIG. 4. Effect of Monoamine Oxidase-B (MAO-B) Inhibitors on Cocaine-Induced Locomotor Sensitization of Mice. FIGS. 4C-4F: Analysis of locomotor sensitization by open-field test upon treatment with deprenyl (C), rasagiline (D), pargyline (E), or lazabemide (F) with or without cocaine. #p<0.05, n=10-12, two-way ANOVA, mean±SEM.

FIG. 5. CGP3466B Prevents Neurotoxic Effects of Cocaine In Vivo.

FIG. 6. Dose dependent responses of CREB and p53 upon treatment with cocaine. Related with FIG. 1.

FIG. 7. Effects of D1 receptor antagonist on GAPDH nitrosylation. Related with FIG. 3.

FIG. 8. Effect of CGP3466B on locomotor sensitization of mice. Related with FIG. 3.

FIG. 9. Effect of MAO-B inhibitors on cocaine induced cell death of mice. Related with FIG. 5.

DETAILED DESCRIPTION OF THE INVENTION

Figure 1A:
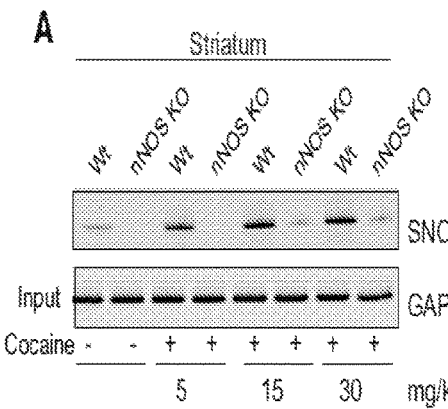
FIGS. 1A and 1B: Levels of nitrosylated GAPDH (SNOGAPDH) in mice receiving behavioral-stimulant doses (A) or neurotoxic doses (B) of cocaine in both wild-type and nNOS knockout (nNOS KO) mice.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present inventors have identified a molecular pathway whereby cocaine exerts its behavioral stimulant and neurotoxic actions by stimulating the formation of nitric oxide (NO) which nitrosylates glyceraldehyde-3-phosphate dehydrogenase (GAPDH) enabling GAPDH to bind to Siah1 and translocate to the nucleus. In the nucleus, the GAPDH-Siah complex binds to the histone methylating enzyme SUV39H1 which is degraded by Siah1 through the ubiquitin E3 ligase activity of Siah1. Following behavioral stimulant doses of cocaine, this process facilitates acetylation of histone H3 leading to CREB binding to DNA with enhanced expression of CREB related genes that lead to behavioral stimulant effects. Following neurotoxic doses of cocaine, in the nucleus nitrosylated GAPDH instead binds to p300/CBP which acetylates and activates p53 leading to cytotoxicity. The present inventors show that drugs which potently and selectively block nitrosylation of GAPDH, such as Deprenyl and CGP3466B, block both behavioral stimulant and neurotoxic pathways to prevent stimulant and neurotoxic actions of cocaine. As other drugs of abuse also stimulate NO formation, they likely act via this pathway. Accordingly, drugs that inhibit nitrosylation of GAPDH and its binding to Siah should prevent behavioral and toxic actions of other drugs of abuse including opiates, stimulants and phencyclidine.

The present invention provides methods and compositions for blocking the behavioral stimulant and/or neurotoxic effects of cocaine. More specifically, drugs that inhibit, block or otherwise prevent the nitrosylation of GAPDH, inhibit GAPDH/Siah binding and/or otherwise prevent the nuclear translocation of GAPDH are useful in the present invention. One could readily screen for agents that selectively block nitrosylation of GAPDH, inhibit GAPDH/Siah binding and/or otherwise prevent the nuclear translocation of GAPDH. See, e.g., U.S. Pat. No. 7,001,738; No. 6,806,057. Moreover, the present invention can be applied to other drugs that act along the pathway described herein.

In particular embodiments, the inhibitor is CGP3466B or a pharmaceutically acceptable salt thereof. This compound is also known as TCH346 or omigapil, and is represented by the formula N-(dibenz(b,f)oxepin-10-ylmethyl)-N-methyl-N-prop-2-ynylamine CGP3466B or salts thereof has been proposed and investigated as a potential treatment option for various neurodegenerative diseases in which cell death plays a role. Such neurodegenerative diseases include cerebral ischemia, Alzheimer's disease, Huntington's disease and Parkinson's disease, amyotrophic lateral sclerosis, multiple sclerosis, types of glaucoma, retina degeneration, as well as general or diabetic peripheral neuropathy. The use of CGP3466B or salts thereof for the treatment of these diseases as well as processes for its preparation are disclosed in WO 2005/044255, WO 2004/066993, WO 97/45422, and EP-A-0726265. See also, U.S. Pat. No. 7,875,648 and Kragten et al., 273 J. BIOL. CHEM. 5821-28 (1998).

In other embodiments, the drug is the monoamine oxidase-B (MAO-B) inhibitor, Deprenyl (also known as selegiline). Deprenyl, including its acid addition salt forms, has been known to be useful for veterinary and clinical purposes because of its neuronal-protective or neuronal-regenerative effects and its dopaminergic effects, i.e., its selective inhibition of the enzymatic degradation of dopamine by monoamine oxidase B. Selegiline, i.e., R-(−)-N-methyl-N-(prop-2-ynyl)-2-aminophenylpropane, also known as L-(−)-deprenyl or R-(−)-deprenyl.

Future work in our laboratory will evaluate possible actions of diverse drugs of abuse upon the NO-GAPDH pathway. As cocaine and amphetamines both act by facilitating the synaptic effects of dopamine, the present inventors are exploring the actions of amphetamines and related stimulants. In recent years abundant evidence has established that the rewarding effects of drugs of abuse ranging from alcohol through barbiturates, opiates and stimulants, act via the dopamine systems of the nucleus accumbens in the brain. Hence, it is reasonable to anticipate that many/most drugs of abuse act via dopamine, like cocaine, and through the NO-GAPDH pathway. Moreover, there is literature indicating that most drugs of abuse stimulate the formation of NO which would also lead to activation of the NO-GAPDH pathway.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Drugs. Cocaine HCl (Sigma-Aldrich) was dissolved in physiological saline. CGP3466B was obtained from Tocris Bioscience and dissolved to 10 mM in water and 100 mM in DMSO (vehicle). Deprenyl (soluble in PBS), Rasagiline (soluble in PBS), Lazabemide (soluble in DMSO), SCH32290 (soluble in PBS), and Pargyline (soluble in PBS) were obtained from Sigma. Antibodies purchased from commercial: c-fos (Santa Cruz, 1:150 dilution), Arc (Santa Cruz, 1:250 dilution), and PUMA (Santa Cruz, 1:250 dilution), CREB (Santa Cruz, 2 mg per 100-500 mg of total protein), and p53 (Santa Cruz, 2 mg per 100-500 mg of total protein).

Sample Preparation from Cocaine-Injected Mice. C57BL/6 mice and nNOS knockout (Jackson) mice were injected once per day (intraperitoneally [i.p.]) with saline or cocaine (0-50 mg/kg) before rapid isolation of striatum 1 hr after injection. Striatum lysates were used to measure nitrosylation of GAPDH by biotin switch assay. Striatum lysates were also used to do western blot hybridization to measure c-fos, Arc, PUMA levels, and ChIP assay to measure CREB and p53 binding to c-fos and PUMA promoter respectively.

Behavioral Testing.

Mice. Male wild-type mice with C57BL/6 genetic background from Jackson laboratories at 10 weeks of age were used for all behavioral testing. All animals were handled according to the Johns Hopkins University School of Medicine Animal Care and Use guidelines.

Open-Field Test. Open-field assessments were conducted as described (Levine et al., 2011; Maze et al., 2010) with brief modifications. The open field is a square arena with the dimensions 47 cm 3 47 cm with a 38.1 cm high clear plastic wall. Activity chambers were computer interfaced for data sampling. Sixteen infrared photobeams in each direction (16×16), 2.77 cm spacing, were used to record movement. The San Diego PAS software recorded the total number of beam breaks, as well as the beam break's location in the center and peripheral areas.

Mice were divided in 5 groups (n=10-12 each). Each group of mice were injected (i.p.) with either CGP3466B or the MAO-B inhibitors deprenyl, rasagiline, lazabemide, and pargyline for 5 days. Mice were allowed to acclimate to the apparatus for 1 hr. After 60 min, mice received saline or cocaine (30 mg/kg of cocaine i.p.), and were returned to the open-field apparatus for a subsequent 75 min in which their activity was recorded. All data was measured in 5 min intervals and aggregated as necessary. Beam breaks or distance traveled for 20 min following cocaine/saline intraperitoneal injection after the first stage of testing were used to determine immediate peak locomotor response from cocaine injection. In between testing of mice, the arena was wiped with Vimoba cleaning solution. Mice were tested at the same time every day in order to minimize any variation due to circadian rhythm changes.

Rotarod Performance. The test was performed as described previously (Xi et al., 2011) with minor modifications. A four-station mouse rotarod device (AccuScan Instruments) was used to study the effects of CGP3466B, Deprenyl, Rasagiline, Lazabemide and Pargyline on cocaine induced operant locomotion in mice. The speed of rotation of the rotarod was increased from 4 to 32 rpm over 7 min.

Mice were divided into 5 groups (n=8). For 5 days prior to testing mice received one dose of deprenyl (0.25 mg/kg), rasagiline (2.5 mg/kg), pargyline (50 mg/kg), lazabemide (50 mg/kg), or saline followed by a high dose of cocaine (50 mg/kg). Mice were placed on the rotarod at a starting speed of 4 rpm, and the speed of the rotarod was increased to 32 rpm over the course of 7 min. This was repeated for a total of three trials in a day, and the latency at which the mice fell off the rotarod was recorded. Mice were tested at the same time every day in order to minimize any variation due to circadian rhythm changes.

Conditioned Place Preference. The test was performed as described previously (Levine et al., 2011; Maze et al., 2010; Xi et al., 2011) with minor modifications. Two groups of wild-type mice were used to study the effect of CGP 3466B (0.15 mg/kg) on cocaine-(7 mg/kg) induced conditioned place preference or aversion. A three-chamber place preference apparatus was used. This apparatus consisted of two large side compartments and one small central compartment, which separated the large compartments. Two of the large compartments had different visual and tactile cues. One of the large compartments contained a green wire mesh floor. The second large compartment contained a cream-colored rubber floor. The small central compartment had a smooth clear Plexiglas floor. A white opaque wall encircled the apparatus in order to block out any other visual cues in the behavioral testing area.

Wild mice were divided into two groups. During the preconditioning phase (day 1), mice were placed in the small central compartment and were allowed to freely explore the entire apparatus for 15 min. Experimental software (Any-Maze Video Tracking System v. 4.72) measured the amount of time each mouse spent in each of the three compartments. Mice that did not show a strong preference for either of the large chambers on day 1 were advanced to the next stage of testing.

For the next 10 days (days 2-11), mice entered the conditioning stage of testing with one session per day. On days 2, 4, 6, 8, and 10, one of the groups received an injection of saline and were then confined into the cream-colored rubber floor compartment for 15 min immediately following injection. The second group received an injection of CGP 3466B (0.15 mg/kg) exactly 2 hr prior to testing and then received a second injection of saline before being confined to the same cream-colored rubber floor compartment for 15 min. The compartment was cleaned with Vimoba in between mice. On days 3, 5, 7, 9, and 11, this same protocol was followed, substituting the saline injection with cocaine (7 mg/kg) before both groups were confined to the green-mesh floor chamber for 15 min. The treatment group continued to receive an intraperitoneal injection of CGP3466B (0.15 mg/kg) exactly 2 hr before receiving the cocaine conditioning injection. Only one session of conditioning was conducted each day. On the probe trial day (24 hr after the last conditioning session), mice were given an injection of saline then were allowed to freely explore the three compartments for 15 min the time spent in each of the compartments was recorded by computer software. CPP score was calculated as time spent in cocaine chamber minus the time spent in saline/CGP3466B treated chamber.

Chromatin immunoprecipitation (ChIP) assay. This assay was performed as described previously (Enwright et al., 2010; Kumar et al., 2005; Tsankova et al., 2004). In brief, intact cells were treated with 2 mM disuccinimidyl glutarate (Pierce) to crosslink protein complexes, then were treated with formaldehyde to link protein to DNA covalently. Cells were lysed, the nucleoprotein complexes sonicated and the crosslinked DNA-protein complexes enriched by immunoprecipitation with specific antibodies. The retrieved complexes were analyzed by PCR amplification to detect and quantify specific DNA targets. For performing the ChIP assay using striatum section of brain we followed the protocol of Chromatin preparation from tissues for chromatin immunoprecipitation (ChIP), provided by Abcam. For real-time PCR we used Brilliant SYBR green master mix (Stratagene) according to the manufacturer's protocol.

Extraction of nuclear and cytoplasmic proteins. Nuclear and cytoplasmic extracts were prepared using Biovision Nuclear/cytosol extraction kit according to the manufacturer's instructions.

Co-Immunoprecipitation. Striatum tissue were lysed in lysis buffer (50 mM Tris pH 7.4, 150 mM NaCl, 0.1%

Chaps, 100 nM deferoxamine and 1 mM EDTA) and homogenized by passing through a 26-gauge needle. Crude lysates were cleared of insoluble debris by centrifugation at 14,000 g. IP buffer (50 mM Tris pH 7.4, 150 mM NaCl, 0.1% Chaps, 100 µM deferoxamine, 1 mM EDTA and 0.1 mg/ml BSA) was added to 100 ng of cell lysates to bring samples to a total volume of 1 ml. Anti-Siah and anti-SUV39H1 antibody and 30 µl of protein G agarose were added and incubated on a rotator at 4° C. The protein G agarose was washed four times with lysis buffer and quenched with 30 µl of SDS sample buffer. Co-immunoprecipitates were resolved by SDS-PAGE and analyzed by western blotting with anti-GAPDH and anti-SUV39H1 antibodies.

Quantitative real-time PCR. This assay was performed as described before (Nott et al., 2008). PCR reactions (25 µl) contained 12.5 µl of PCR Sybr Green mix (NEB) with 0.3 µM primers. At the end of the 35 cycles of amplification, a dissociation curve was performed in which Sybr Green was measured at 1° C. intervals between 50° C. and 100° C. Results were normalized using total input DNA and expressed as bound/Input (percentage).

S-nitrosvlation biotin switch assay. Primary neurons overexpressed with dopamine transporter (DAT) were treated with cocaine with or without treatment with deprenyl, rasagaline, lazabemide or pargyline for 16 hr. Then cells were lysed and lysates were used for biotin switch assay to detect nitrosylation of GAPDH (SNO-GAPDH). The assay was performed as described (Jaffrey et al., 2001). In brief, cells were lysed, and reduced cysteines blocked with 4 mM methyl methanethionsulphonate (MMTS). Subsequently, S-nitrosylated cysteines were reduced with 1 mM ascorbate and biotinylated with 1 mM Biotin-HPDP (Pierce, Rockford, Ill.). The biotinylated proteins were pulled down with streptavidin agarose and analyzed by western blotting.

TUNEL assay. Primary neurons were grown on coverslips with a density of 2×105 per 12-well. Cells were treated with deprenyl (2 µM), rasagaline (10 µM), lazabemide (10 µM) or pargyline (10 µM) for 16 hr and cell death was measured by TUNEL assays using TUNEL enzyme (Roche) and TUNEL label (Roche) following the manufacturer's instructions (Kickstein et al., 2010). To analysis cell death induced by neurotoxic dose of cocaine, we used TUNEL apoptosis detection kit (Millipore) using manufacturer's protocol (Lathia et al., 2010). Positive nuclei were counted in 30 fields (×400) for each slide.

Lentiviral injections in mice brain. The stereotaxic injections (David Kopf Instruments, Tujunga, Calif.; n=3 per group) were performed under pentobarbital anesthesia (45 mg/kg, i.p.) using a syringe (Hamilton, Reno, Nev.) with a 30 gauge blunt-tip needle (de Almeida et al., 2002). Lentiviral vectors expressing the wild-type GAPDH or mutant C150S GAPDH were injected in the left or the right striatum, respectively. The animal received 4 µl injections of lentiviral vectors in each side at the following coordinates: 1.0 and 0.0 rostral to bregma, 3.0 and 3.3 lateral to mid-line, and 5.0 ventral from the skull surface, with the mouth bar set at 3.3. The viruses were injected at 0.2 µl/min by means of an automatic injector (Stoelting Co.), and the needle was left in place for 5 min. The skin was closed using a 6-0 Vicryl suture (Ethicon; Johnson & Johnson, Brussels, Belgium). Three animals were killed, and the brains processed for both immunofluorescence and western blot hybridization 10 days after injection to confirm expression of HA-GAPDH. Mice overexpressing either HA-GAPDH or HA-C150S GAPDH were treated with cocaine with both behavioral and neurotoxic doses as mentioned before. Then mice were sacrificed and striatum was isolated from each animal. Striatum lysates were used to perform various western blots and ChIP analyses.

Statistical analysis. Data are expressed as mean±standard error (SE). Statistical significance of differences between 2 groups was determined by unpaired two tailed t-test, and between 3 or more groups by a one-way analysis of variance (ANOVA), two-way ANOVA or an ANOVA with repeated measures followed by the Tukey-Kramer post-hoc correction for multiple comparisons. $p<0.05$ was regarded as statistically significant.

Results

Figure 1B:
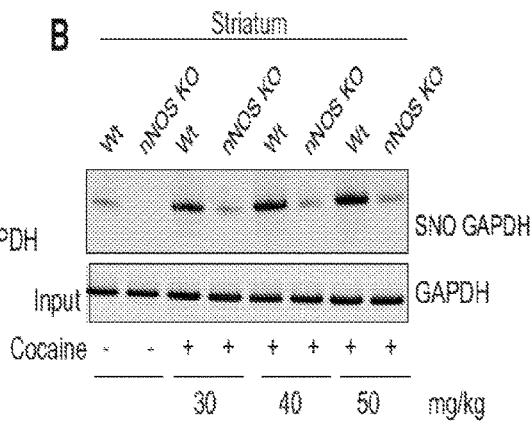

Nitrosylated GAPDH Contributes to Both Behavioral and Neurotoxic Effects of Cocaine. To determine a role for the NO-GAPDH cascade in cocaine actions, we treated mice with single behavioral-stimulant doses of cocaine (5-30 mg/kg; FIG. 1A) or a neurotoxic regimen of 5 doses of cocaine (30-50 mg/kg), monitoring nitrosylation (FIG. 1B) of GAPDH (SNO-GAPDH) in mice with targeted deletion of nNOS. Both stimulant and neurotoxic treatment protocols of cocaine augment levels of nitrosylated GAPDH, with the neurotoxic protocol eliciting a larger effect. All these influences of cocaine are virtually abolished in nNOS knockout mice, establishing that cocaine impacts this signaling pathway.

Figure 6A:
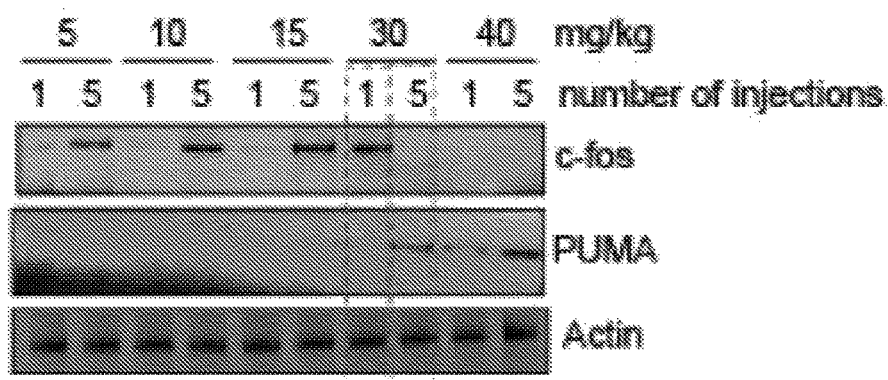
FIG. 6A: Analysis of c-fos and PUMA levels with various doses of cocaine.
Figure 6B:
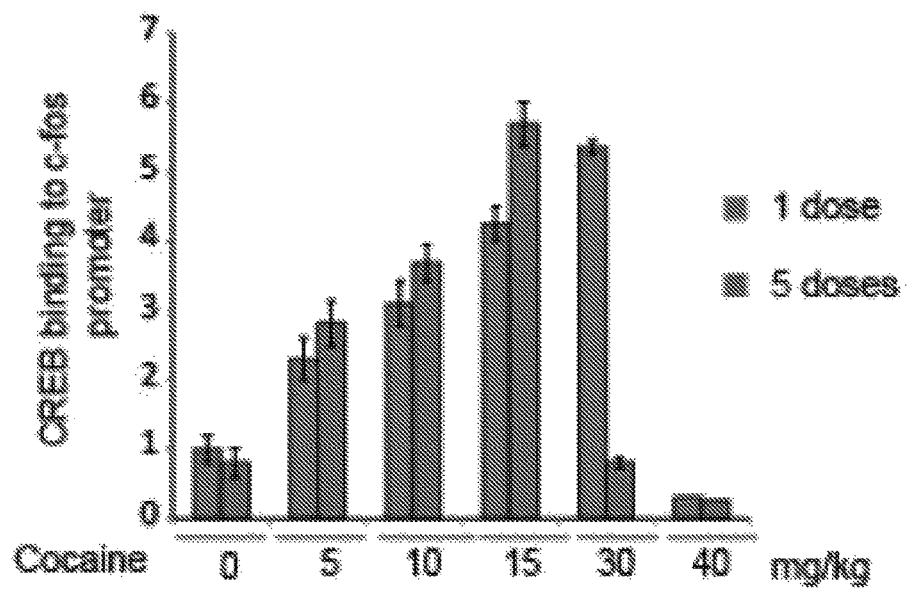
FIG. 6B: ChIP analysis to measure CREB binding to the c-fos promoter.
Figure 6C:
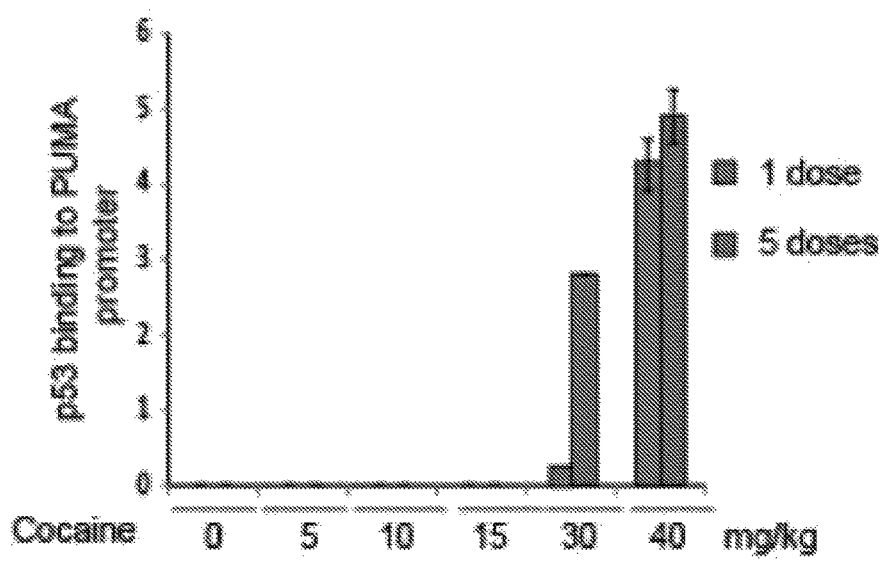
FIG. 6C: ChIP analysis to measure p53 binding to the PUMA promoter.

To discriminate effects of dose and dosing scheduled, we administered single 5-40 mg/kg doses as well as multiple treatments with these doses. Single doses of cocaine (5-30 mg/kg) induce CREB binding to the c-fos promoter (see FIG. 6A) with increases in c-fos protein levels (FIG. 6B). By contrast, treatment with 40 mg/kg cocaine, either in single or multiple doses, induces p53 binding to the PUMA promoter (FIG. 6C), with attendant increases in PUMA protein levels (FIG. 6B). Administering 30 mg/kg cocaine for 5 days induces PUMA (FIG. 6B, red dotted box), while single doses of 30 mg/kg cocaine induce c-fos level (FIG. 6B, blue dotted box). Accordingly, single doses of cocaine (5-30 mg/kg) were used to study behavioral effects of cocaine and 40 mg/kg cocaine was employed as a neurotoxic dose. Mice receiving 30 mg/kg cocaine for 5 consecutive days were also used to study cocaine-associated cell death.

Figure 1C:
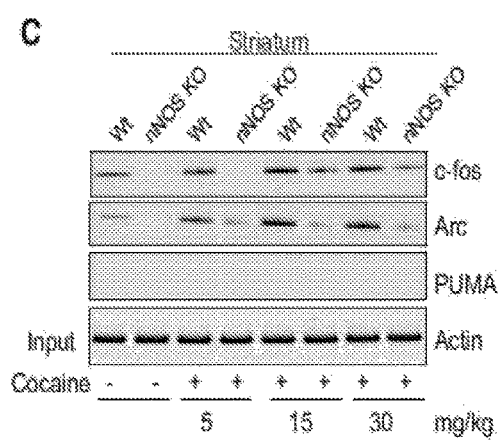
FIGS. 1C and 1D: Differential expression of c-fos, BDNF, Arc, PUMA, and Bax proteins with behavioral doses (C) or neurotoxic doses (D) of cocaine.
Figure 1D:
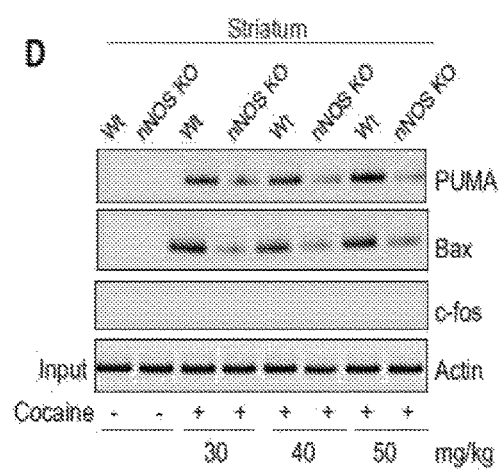
Figure 1:
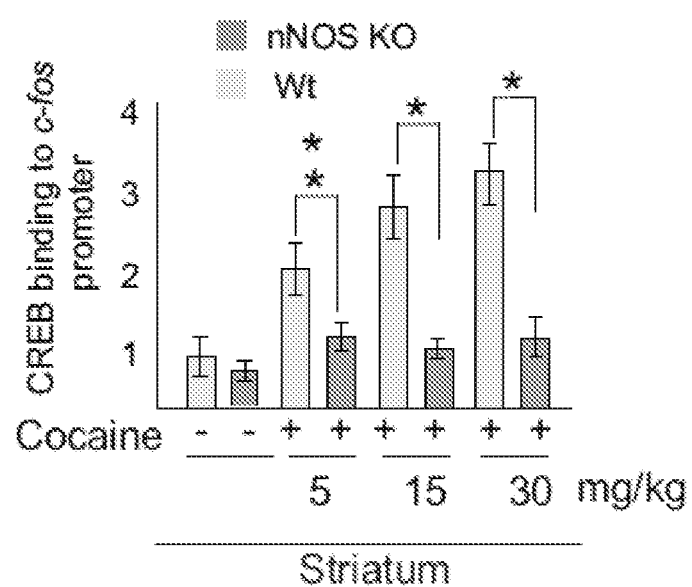
FIG. 1. Neuronal NO Mediates Cocaine's Enhancement of p53 and CREB Gene Transcription.

Earlier, we reported that NO-GAPDH signaling initiates a cascade leading to nuclear transcription of p53 and CREB targets (Sen et al., 2008; Sen and Snyder, 2011). The stimulant cocaine regimen augments levels of c-fos and the immediate early gene Arc but not PUMA, and these effects are lost in nNOS knockout mice (FIG. 1C). By contrast, the neurotoxic cocaine regimen enhances levels of PUMA and Bax but not c-fos with these actions absent in nNOS mutants (FIG. 1D).

Figure 1F:
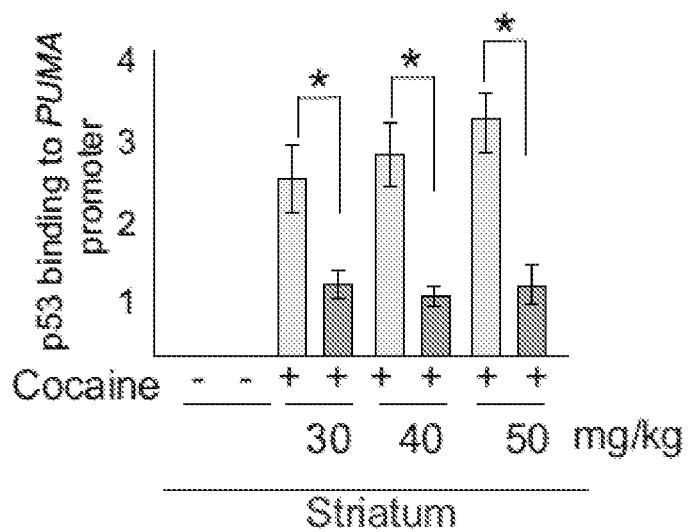

Utilizing ChIP assays, we monitored CREB binding to the c-fos promoter with stimulant doses of cocaine (FIG. 1E) and p53 binding to the PUMA promoter with the neurotoxic regimen (FIG. 1F). CREB-c-fos promoter binding is markedly increased by stimulant doses of cocaine, effects abolished in nNOS knockouts (FIG. 1E). The neurotoxic cocaine regimen greatly increases p53 binding to the PUMA promoter, effects which are lost in nNOS knockouts (FIG. 1F).

Figure 2A:
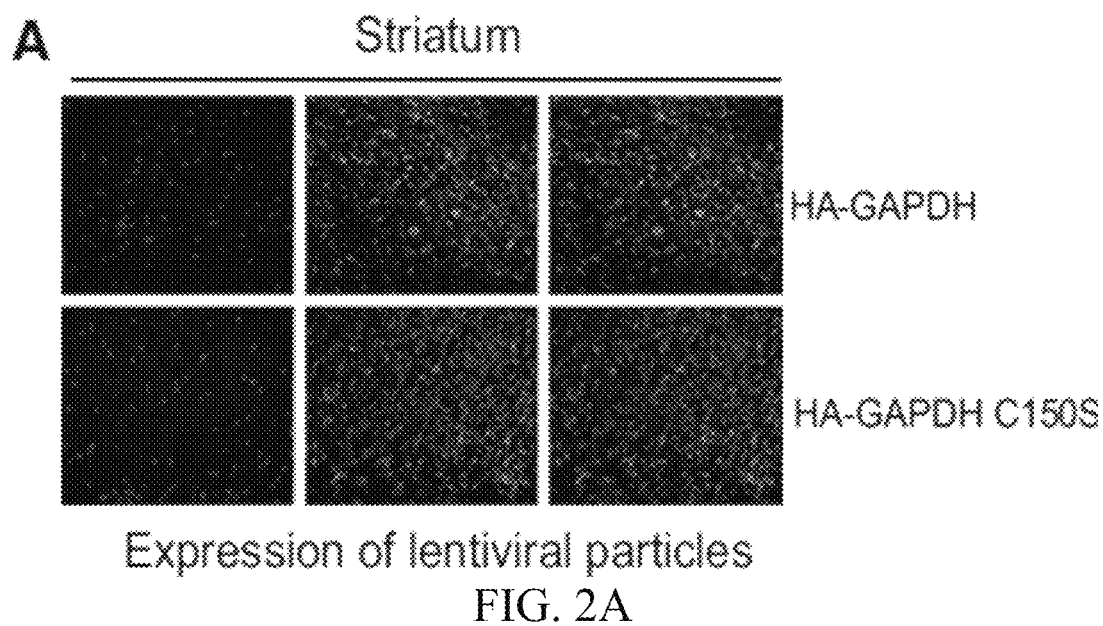
FIG. 2A: Confocal microscopic analysis of the intrastriatal injection of lentiviral particles of HAGAPDH and HA-C150S GAPDH in mice brain.
Figure 2B:
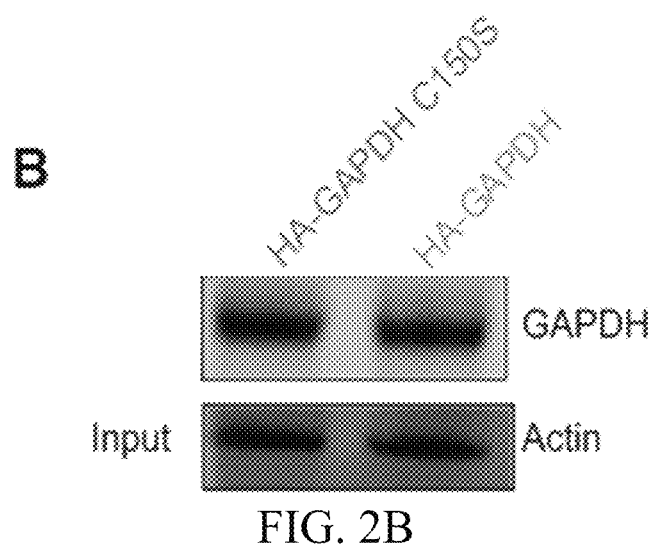
FIG. 2B: Western blot analysis to detect overexpression of HA-GAPDH and HA-C150S GAPDH in brain.
Figure 2C:
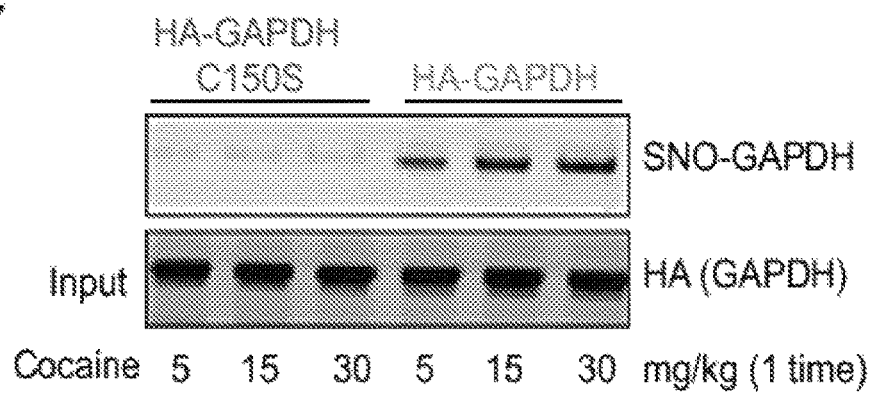
FIG. 2C: Level of nitrosylation of GAPDH (SNO-GAPDH) in striatum of mice receiving single injections of cocaine (5-30 mg/kg).
Figure 2D:
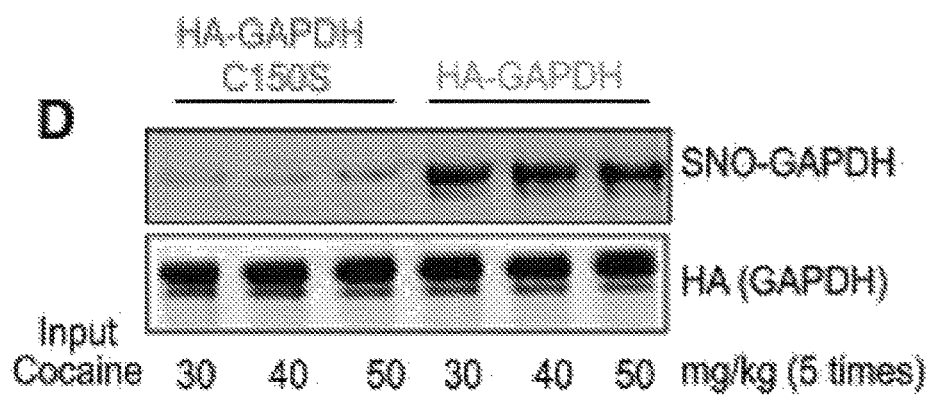
FIG. 2D: Level of nitrosylation of GAPDH (SNO-GAPDH) in striatum of mice receiving cocaine (30-50 mg/kg for 5 days).
Figure 2E:
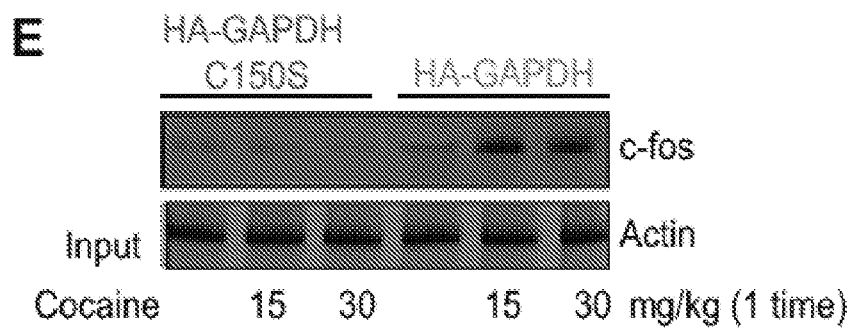
FIGS. 2E and 2F: Levels of c-fos (E) and CREB binding to c-fos promoter (F) were measured in mice overexpressing HA-GAPDH or HA-C150S GAPDH in striatum.
Figure 2F:
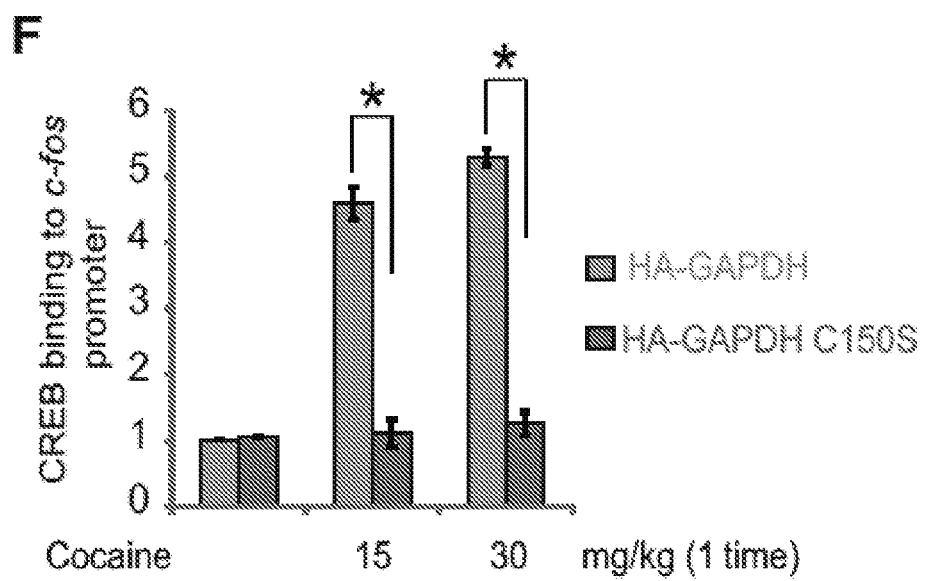
Figure 2G:
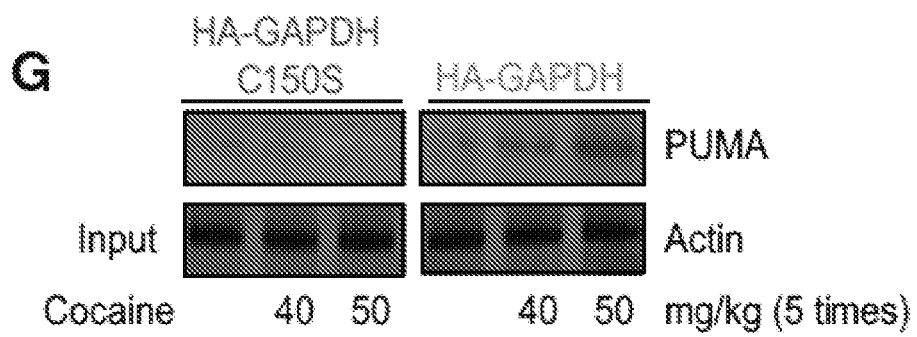
FIGS. 2G and 2H: PUMA protein level (G) and p53 binding to PUMA promoter (H) were measured in mice overexpressing GAPDH or GAPDH-C150S in striatum. *p<0.01, n=3, one-way ANOVA, mean±SEM.
Figure 2H:
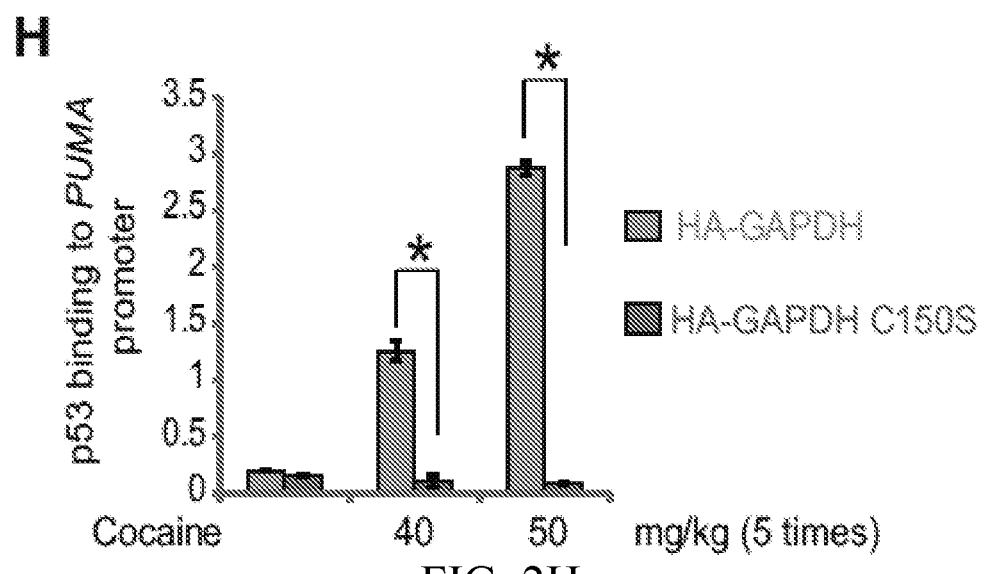

Nitrosvlation of GAPDH is Required for Cocaine Actions In Vivo. Loss of cocaine actions in nNOS knockout mice establishes a role for neuronal NO under these influences. To assess more directly whether effects of cocaine are specifically mediated by GAPDH nitrosylation, we administered lentiviral particles of wild-type GAPDH and C150S mutant of GAPDH-which cannot be nitrosylated-into the striatum of mice brain. Expression levels of both constructs are the same (FIGS. 2A and 2B). After overexpression of these constructs, we treated mice with single behavioral-stimulant doses of cocaine (5-30 mg/kg) or a neurotoxic regimen of 5 doses of cocaine (30-50 mg/kg) and monitored nitrosylation of GAPDH. Nitrosylation of wild-type but not C150S mutant GAPDH is observed after treatment with both behavioral and neurotoxic doses of cocaine (FIGS. 2C and 2D). As expected, CREB binding to the c-fos promoter and levels of c-fos are increased in mice overexpressing wild-type GAPDH but not GAPDH C150S (FIGS. 2E and 2F). Similarly, with neurotoxic doses of cocaine, p53 binding to the PUMA promoter and PUMA protein levels are enhanced in mice overexpressing wild-type GAPDH (FIGS. 2G and 2H). This suggests that nitrosylation of GAPDH mediates both behavioral and neurotoxic doses of cocaine significantly.

Figure 3A:
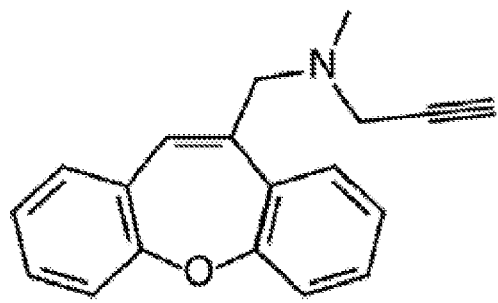
FIG. 3A: Structure of CGP3466B.
Figure 3B:
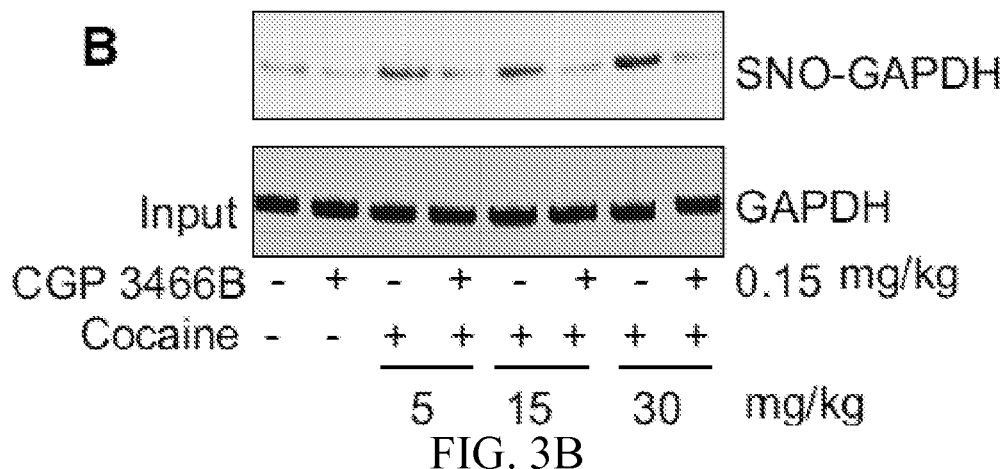
FIGS. 3B and 3C: CGP3466B decreases nitrosylation level of GAPDH (B) and nuclear translocation of GAPDH (C) in striatum of cocaine-treated mice.
Figure 3C:
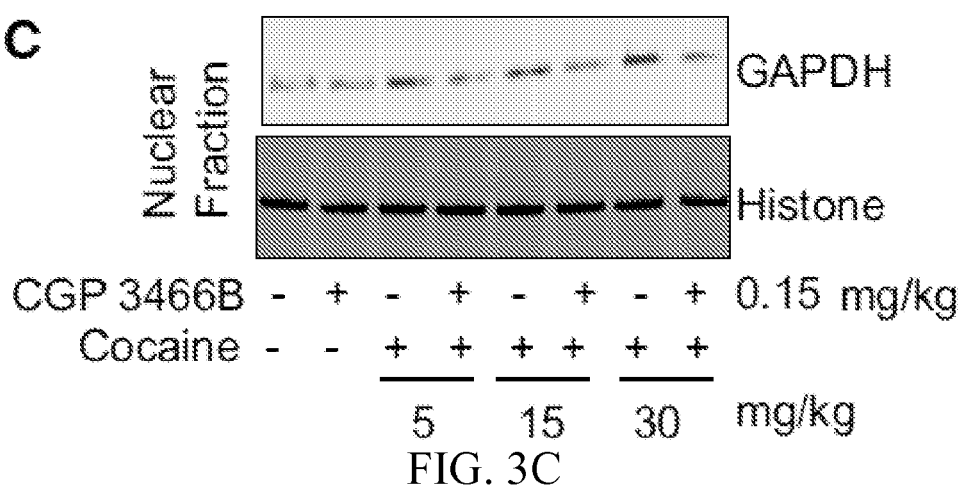
Figure 3D:
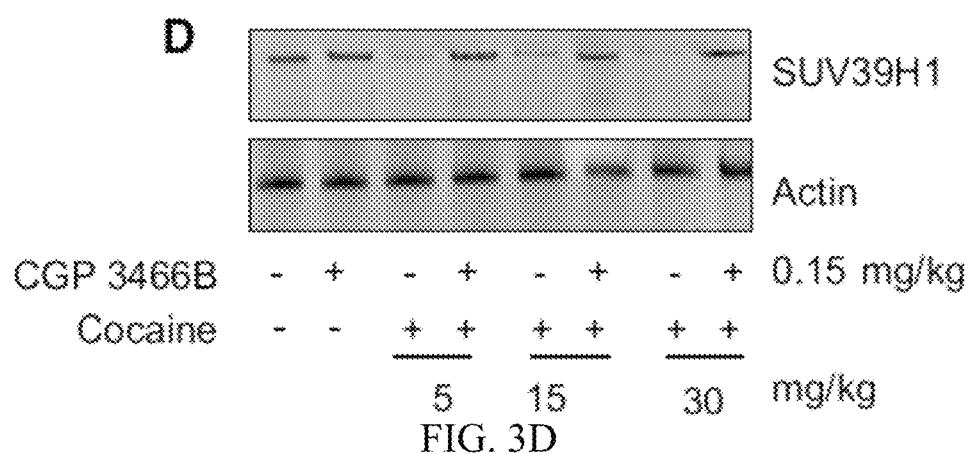
FIGS. 3D and 3E: CGP3466B prevented cocaine-elicited degradation of SUV349H1 (D) and H3K9 trimethylation (E) in striatum.
Figure 3E:
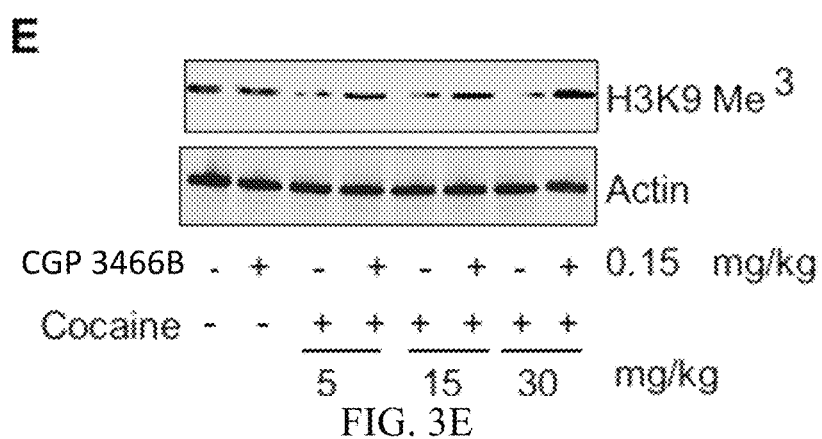
Figure 3F:
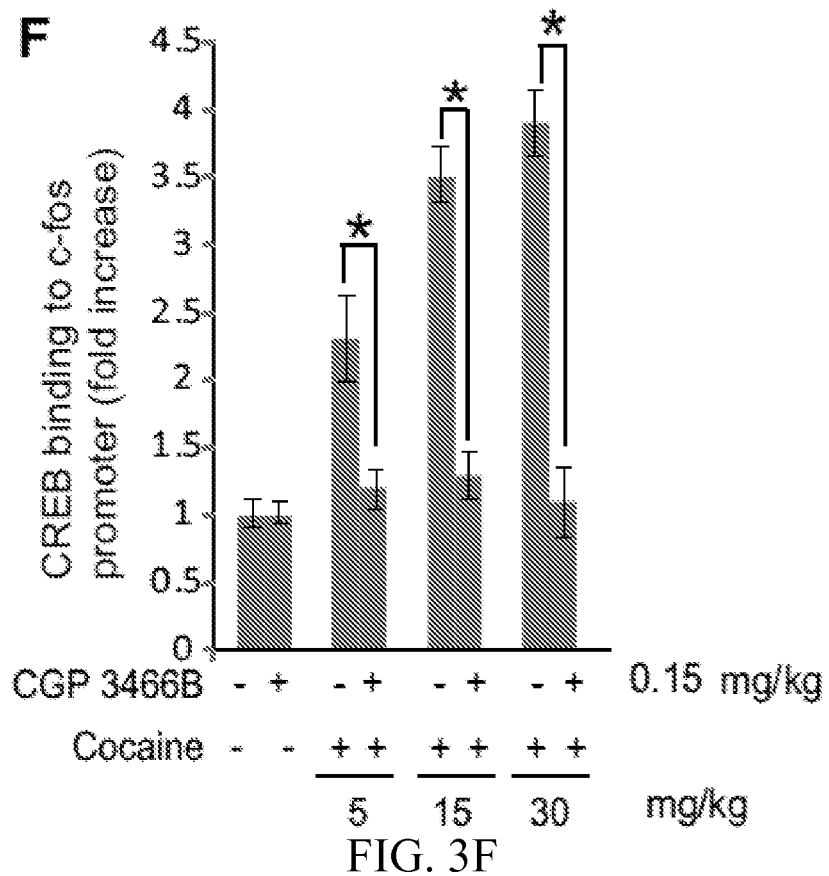
FIGS. 3F and 3G: Analysis of CREB binding to c-fos promoter (F) and c-fos and PUMA levels (G) in mice receiving cocaine with or without CGP3466B.
Figure 7A:
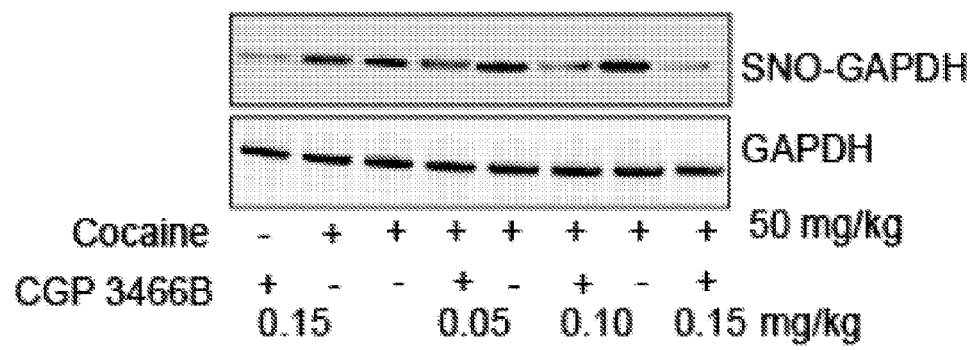
FIG. 7A: Analysis of nitrosylation of GAPDH (SNO-GAPDH) in mice treated with cocaine alone or with cocaine and various doses of CGP3466B.
Figure 7B:
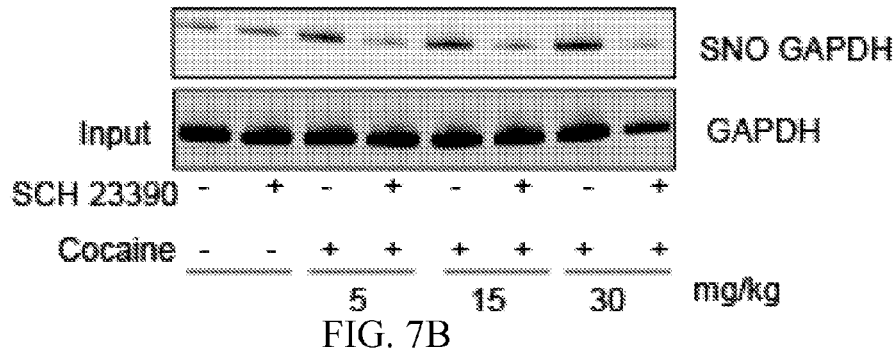
FIGS. 7B and 7C: The D1 receptor antagonist (SCH23390) prevents the stimulation of GAPDH nitrosylation by cocaine, establishing that cocaine's effects reflect dopamine acting at D1 receptors.

Effects of CGP3466B on Behavioral Effects of Cocaine. We sought pharmacologic means to interrupt the cocaine-NOGAPDH signaling system in intact animals. The monoamine oxidase inhibitor deprenyl is known to be neuroprotective (The Parkinson Study Group, 1989; Hara et al., 2006; Sagot et al., 2000; Waldmeier et al., 2000). Derivatives of deprenyl, such as CGP3466B (FIG. 3A), lack monoamine oxidase inhibitory activity but retain neuroprotective effects (Hara et al., 2006). CGP3466B prevents the nitrosylation of GAPDH with extraordinary potency, acting in subnanomolar concentrations, with resultant inhibition of GAPDH binding to Siah1 and nuclear translocation of GAPDH. Behavioral-stimulant doses of cocaine (5-30 mg/kg) increase GAPDH nitrosylation in the corpus striatum—the site of highest dopamine levels in the brain-in a dose-dependent fashion (FIG. 3B). Administration of 0.15 mg/kg CGP3466B almost completely blocks the stimulation of GAPDH nitrosylation in striatum elicited by cocaine (FIG. 7A). CGP3466B also prevents the cocaine-elicited nuclear translocation of GAPDH (FIG. 3C).

Figure 7C:
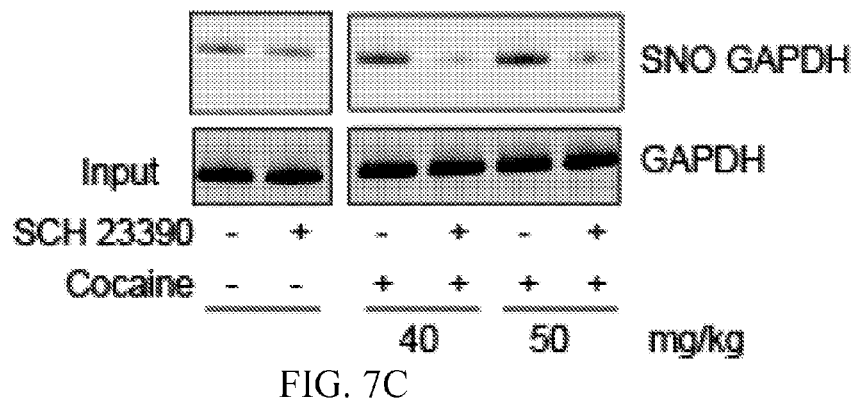

Behavioral actions of cocaine are thought to involve augmented synaptic actions of dopamine upon D1 receptors and are typically blocked by the D1 antagonist SCH23390 (Noda and Nabeshima, 2004). Stimulation of GAPDH nitrosylation both by stimulant (FIG. S2B) and neurotoxic (FIG. 7C) cocaine regimens is blocked by SCH23390 administration. Thus, the NO-GAPDH signaling pathway, like behavioral influences of cocaine, is mediated by dopamine signaling through D1 receptors.

Figure 3G:
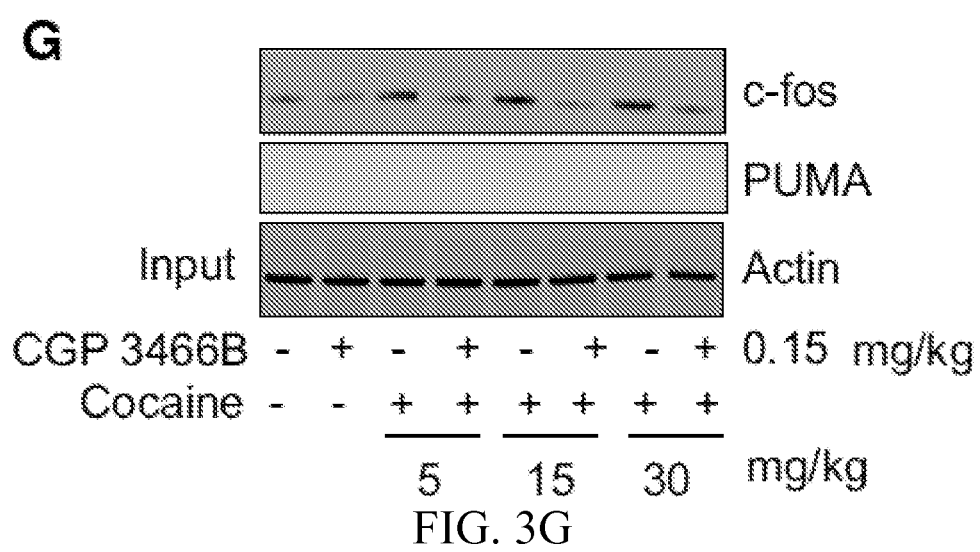
Figure 8A:
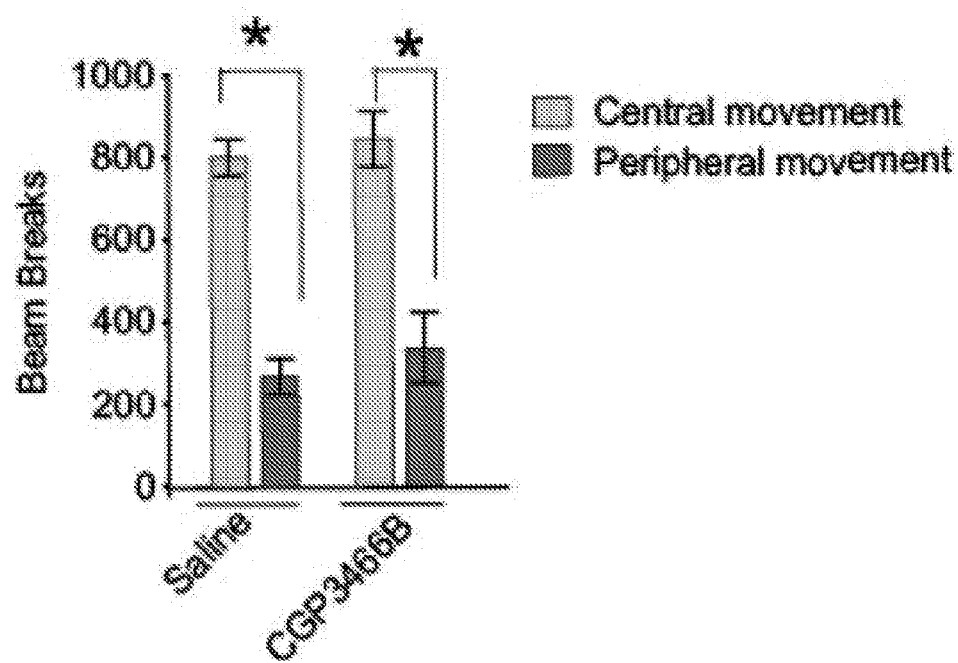
FIG. 8A: CGP3466B has no effect on the distribution of central and peripheral movement by mice. Data were derived from open field test. *p<0.01, n=12, one-way ANOVA, mean±SEM.
Figure 8B:
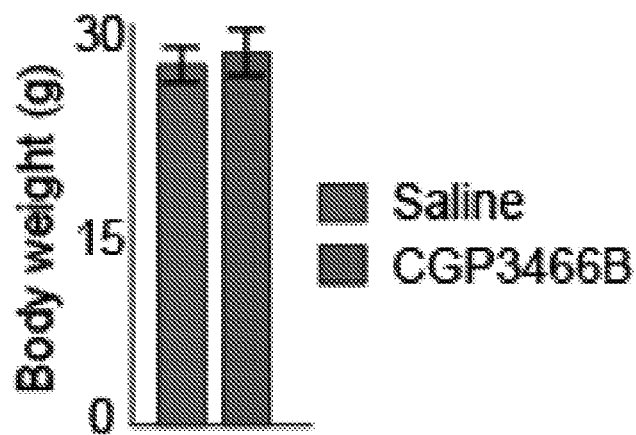
FIG. 8B: CGP3466B has no effect on body weight of mice.
Figure 8C:
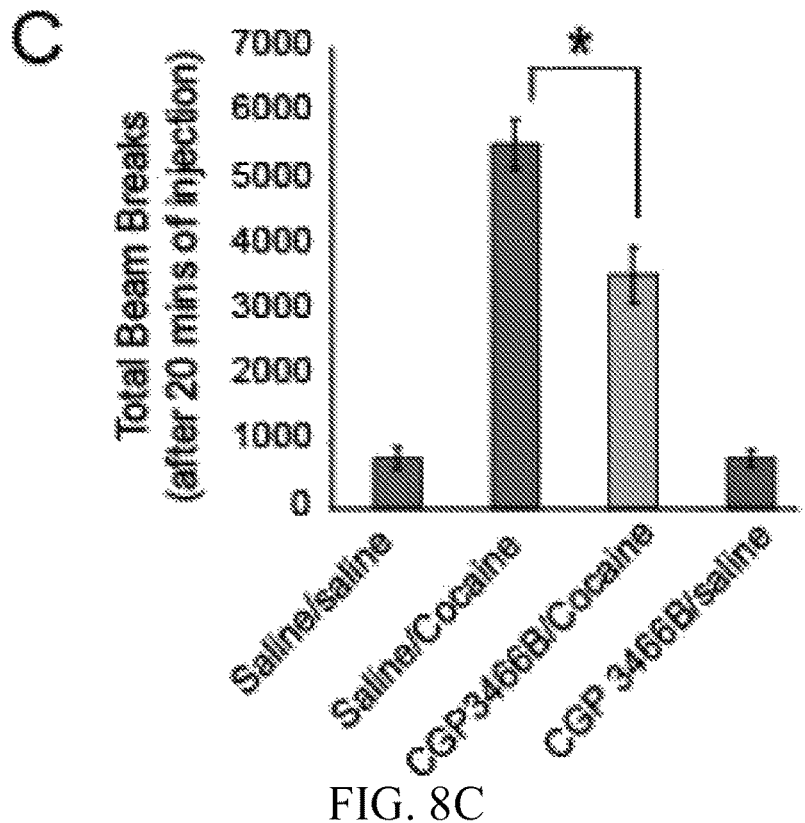
FIGS. 8C and 8D: Total beam breaks (C) and total distance traveled (D) were measured in mice treated with cocaine alone or with cocaine and CGP3466B treatment. *p<0.01, n=12, one-way ANOVA, mean±SEM.
Figure 8D:
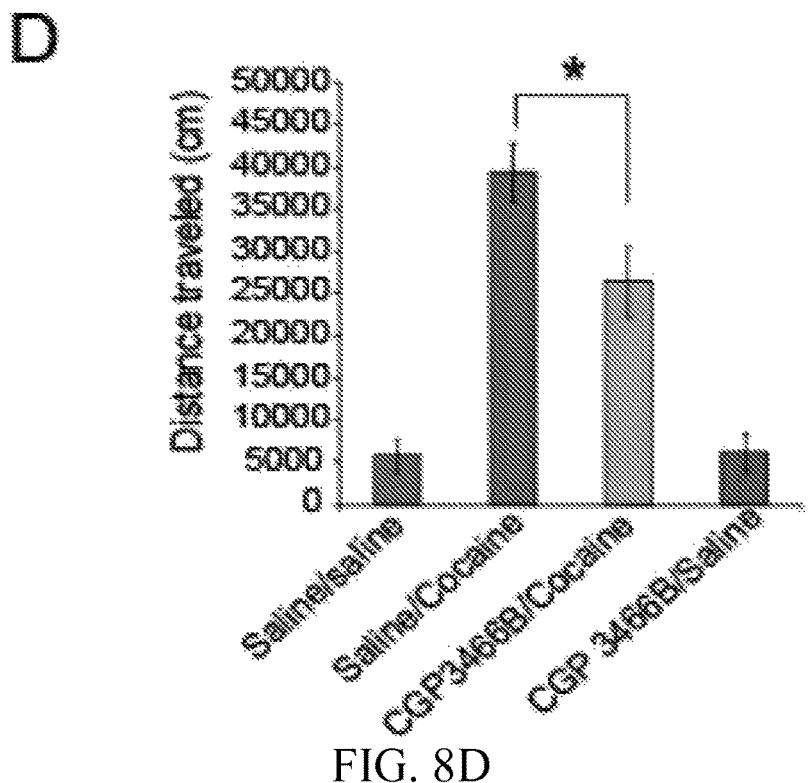

With physiologic stimuli, such as the neurotrophic factors, BDNF and NGF, the nuclear complex of nitrosylated GAPDH linked to Siah1 and the histone methylating enzyme SUV39H1 triggers degradation of SUV39H1 via the ubiquitin E3 ligase activity of Siah1 (Sen and Snyder, 2011). This facilitates enhanced expression of CREB regulated genes such as c-fos. Behavioral-stimulant doses of cocaine enhance nuclear degradation of SUV39H1 (FIG. 3D), with attendant decreased histone methylation (FIG. 3E) and increased transcriptional activation of CREB (FIG. 3F) as well as augmented expression of c-fos (FIG. 3G). Administration of CGP3466B blocks degradation of SUV39H1 and stimulation of c-fos expression (FIGS. 3D-3G). CGP3466B has no adverse effects on central or peripheral movement (FIG. 8A) or body weight (FIG. 8B) of mice.

Figure 3H:
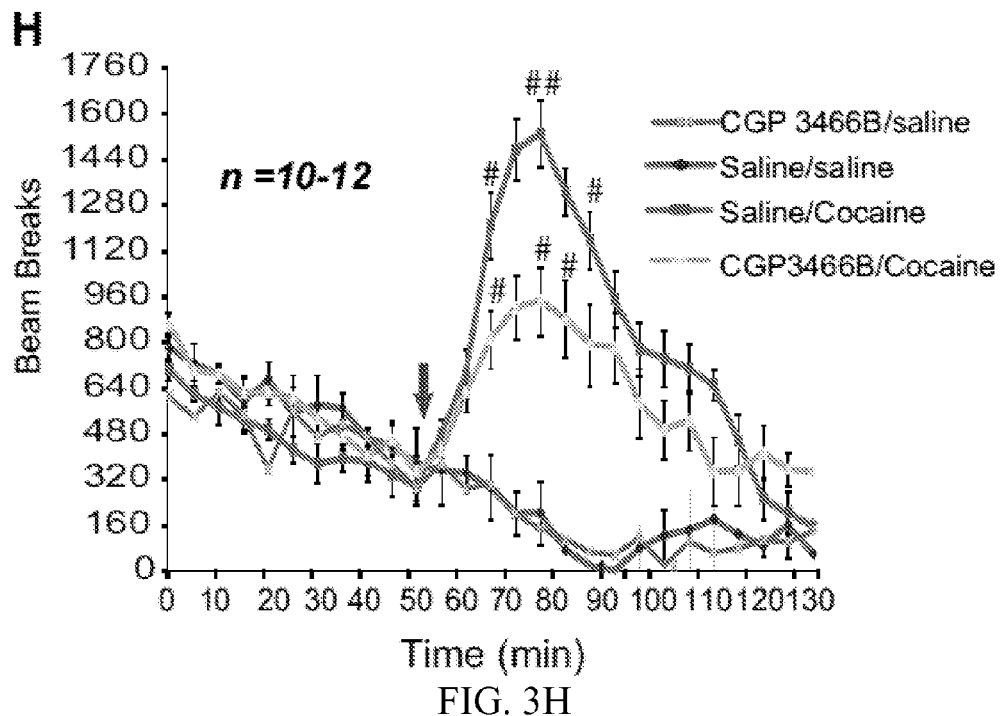
FIG. 3H: Locomotor sensitization of mice monitored in open field test upon treatment with cocaine and CGP3466B. #p<0.05, n=10-12, two-way ANOVA, mean±SEM.
Figure 3I:
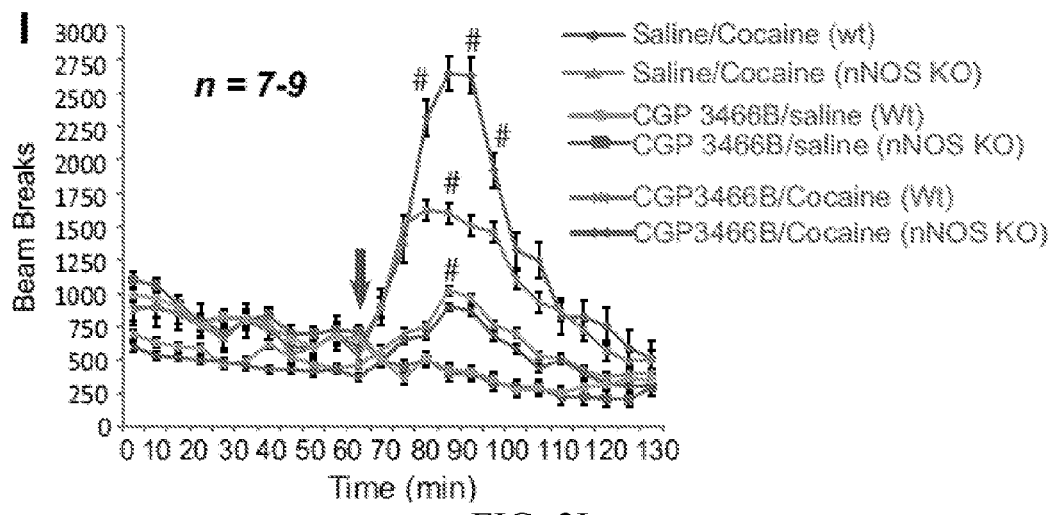
FIG. 3I: Locomotor sensitization of wild-type versus nNOS knockout mice upon treatment with cocaine and CGP3466B, monitored via open-field test. #p<0.05, n=7-9, two-way ANOVA, mean±SEM.
Figure 3J:
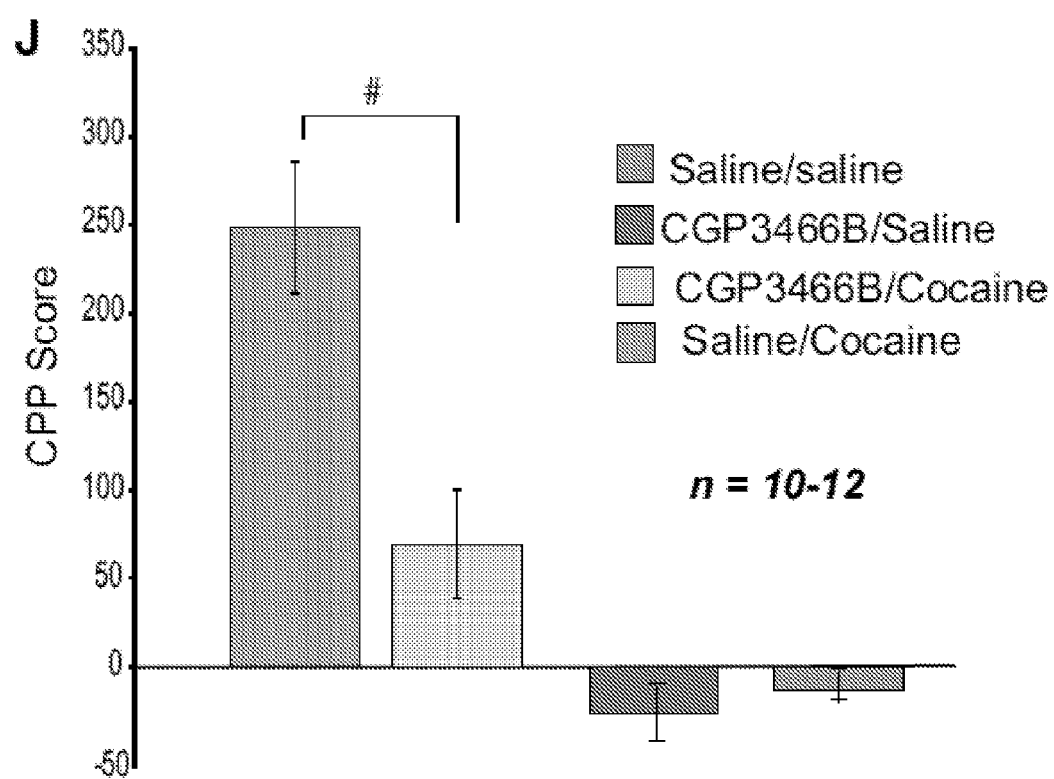
FIG. 3J: Conditioned place preference performance in mice receiving cocaine with or without CGP3466B. #p<0.05, n=10-12, two-way ANOVA, mean±SEM. See also FIGS. 7 and 8.
Figure 6D:
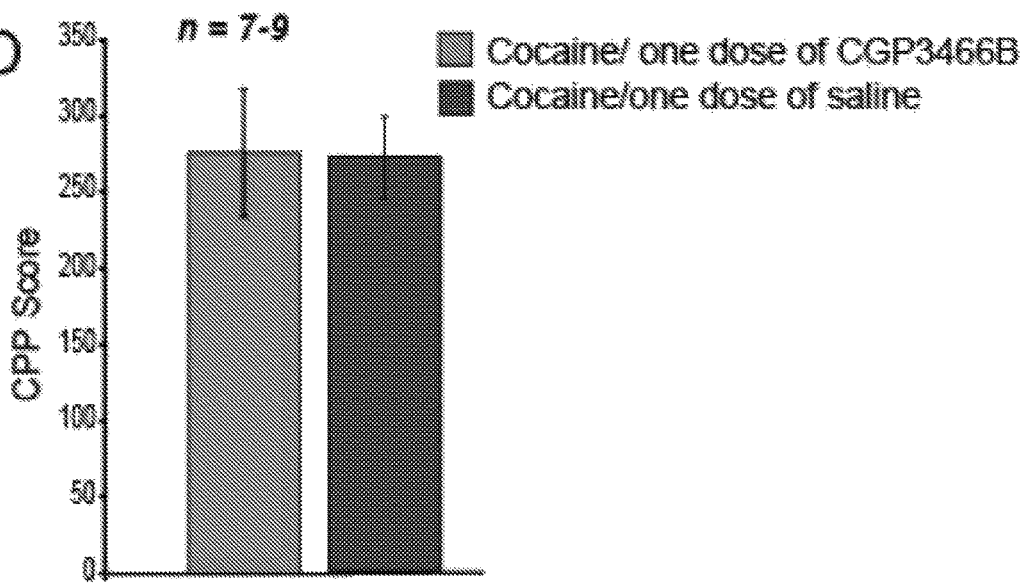
FIG. 6D: Treatment of cocaine-pretreated mice with one dose of CGP3466B on trial day does not alter the conditioned place preference score, which is calculated as the time spent in cocaine chamber minus time spent in saline/CGP3466B chamber.

We investigated whether the NO-GAPDH-CREB system mediates behavioral-stimulant effects of cocaine. CGP3466B was administered at 0.15 mg/kg IP once a day for 5 days with cocaine injected on the fifth day at the same time as the last dose of CGP3466B. We monitored locomotor stimulation by cocaine in an open field model (FIG. 3H, S3C, and S3D). CGP3466B (0.15 mg/kg) substantially reduces locomotor stimulation by cocaine while having no effect on basal locomotor activity. Cocaine induced locomotor stimulation is virtually abolished in nNOS KO mice, consistent with participation by NO in cocaine's actions (FIG. 3I). Administering CGP3466B to nNOS knockout mice treated with cocaine does not further decrease locomotor stimulation, implicating nitrosylation of GAPDH in the behavioral responses (FIG. 3I). To evaluate behavioral preference for cocaine, we employed the conditioned place preference paradigm, with cocaine preference reduced by CGP3466B treatment (FIG. 3J). In this experiment, mice received CGP3466B during the preconditioning stage of the test. When mice were conditioned to the chamber in the absence of CGP3466B, treatment with single dose of CGP3466B only on the day of testing failed to alter conditional place preference (FIG. 6D).

Figures 4A, 4B:
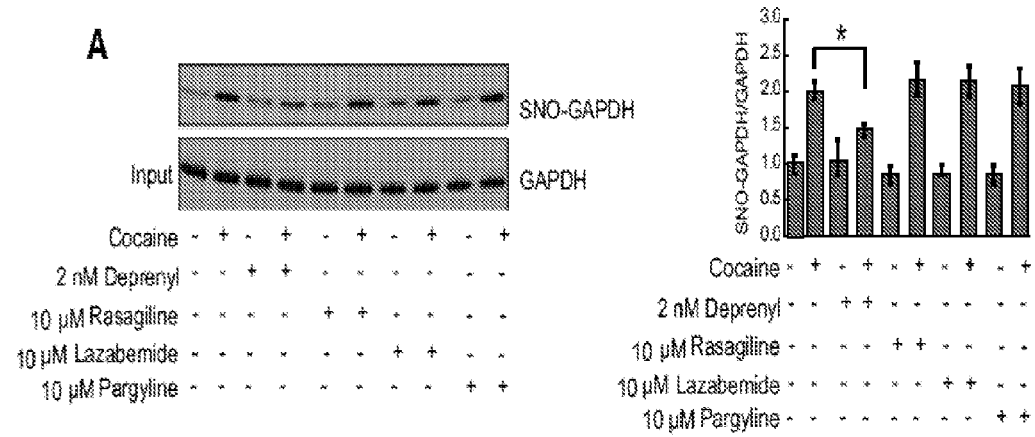
FIG. 4A: Analysis of nitrosylation of GAPDH in primary cortical neuronal cells treated with the MAO-B inhibitors deprenyl, rasagiline, lazabemide, or pargyline.
FIG. 4B: Treatment with deprenyl, rasagiline, lazabemide, or pargyline has no effect on cell survival of primary cortical neurons.
Figure 4C:
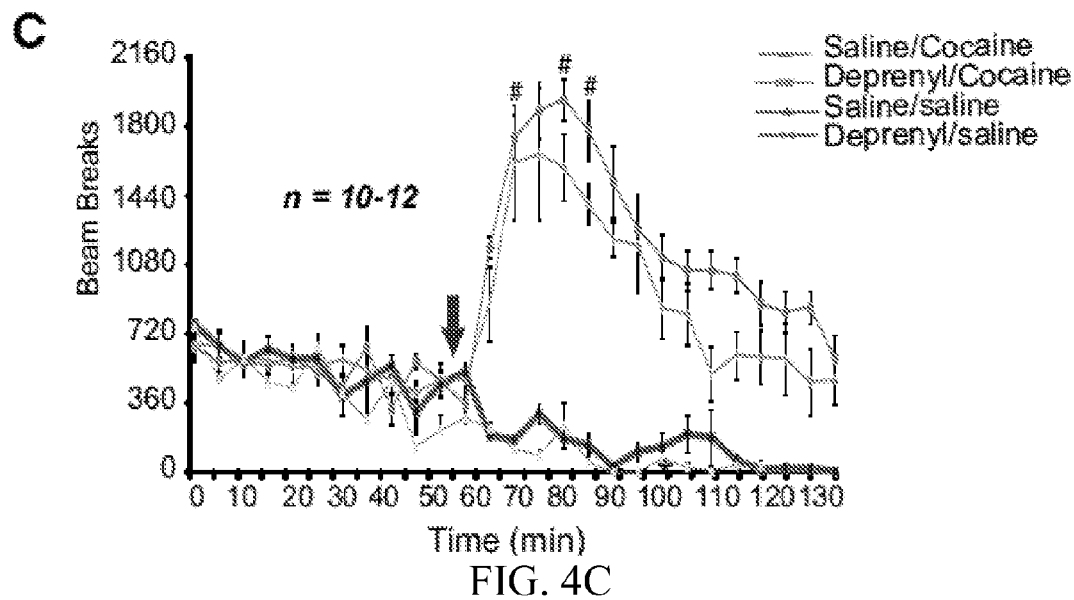
Figure 4D:
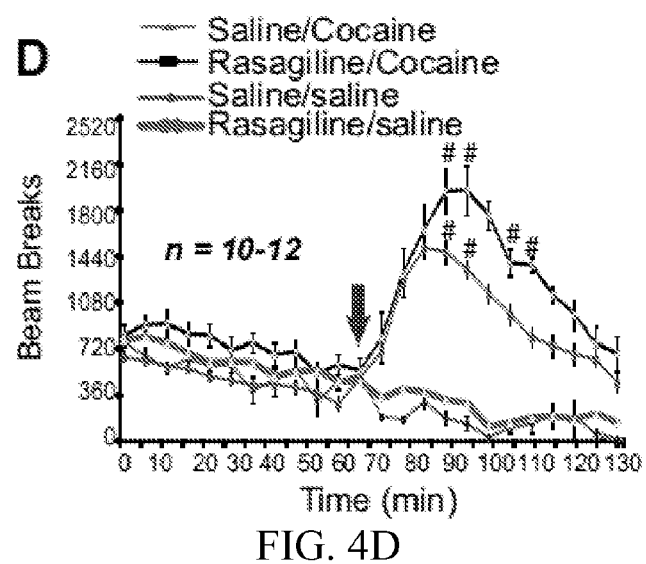
Figure 4G:
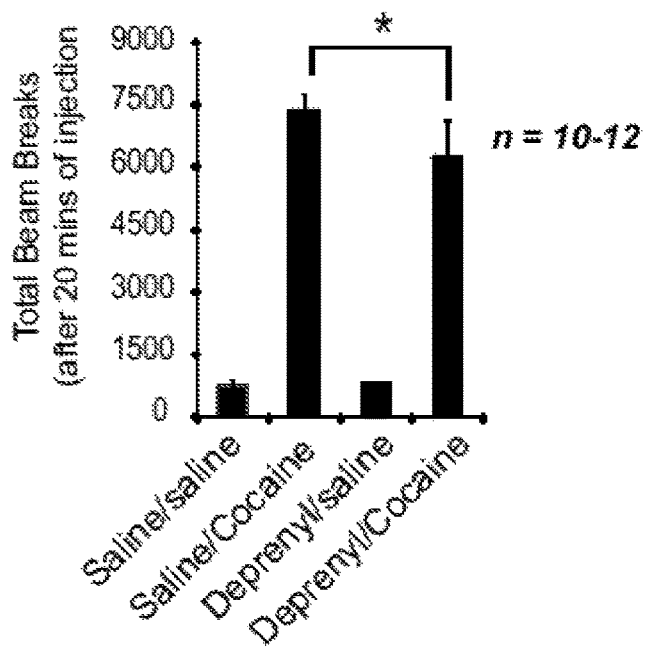
FIGS. 4G and 4H: Total beam breaks were measured in mice treated with cocaine alone or with cocaine and deprenyl (G), rasagiline, lazabemide or pargyline (H). *p<0.01, n=10-12, one-way ANOVA, mean±SEM.
Figure 4H:
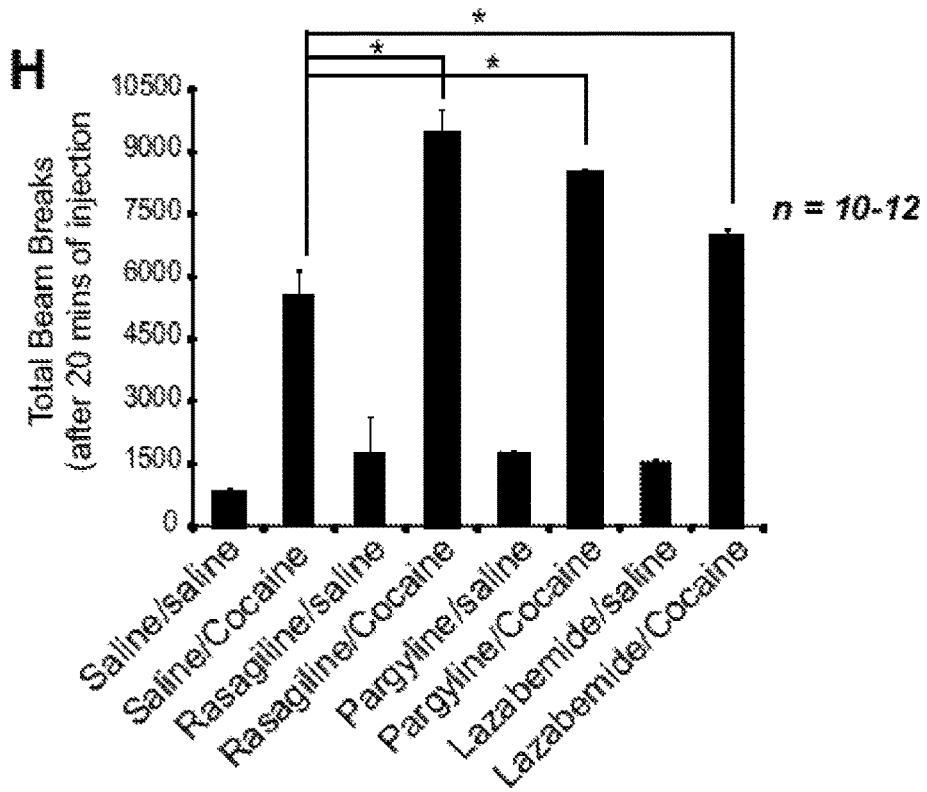

Effects of MAO-B Inhibitors on Behavioral Actions of Cocaine. As reported earlier (Hara et al., 2006), the MAO-B inhibitor deprenyl, like CGP3466B, potently inhibits GAPDH nitrosylation both in vitro and in the brains of mice treated with the neurotoxic agent 1-methyl-4-phenyl-1,2,3,6-tetrahydropyridine (MPTP). In cortical cultures, 2 nM deprenyl, like CGP3466B, prevents cocaine-induced nitrosylation of GAPDH (FIG. 4A). Other monoamine oxidase inhibitors such as rasagiline, lazabemide, and pargyline do not prevent GAPDH nitrosylation. None of these MAO-B inhibitors effects cell death in primary cortical neurons (FIG. 4B). We wondered whether deprenyl, by inhibiting GAPDH nitrosylation, would, like CGP3466B, decrease behavioral effects of cocaine (FIG. 4C). However, monoamine oxidase inhibitors prevent the destruction of dopamine, and of themselves, elicit locomotor stimulation (FIGS. 4D-4F). To discriminate the NO-GAPDH actions from the effects of monoamine oxidase inhibition, we compared locomotor influences of deprenyl with the other monoamine oxidase inhibitors (FIGS. 4G and 4H). Deprenyl significantly decreases cocaine's locomotor activation, though to a lesser extent than CGP3466B. By contrast, rasagiline, pargyline, and lazabemide, when combined with cocaine, elicit greater locomotor stimulation than cocaine alone. Thus, deprenyl, as well as CGP3466B, appears to reduce locomotor stimulant effects of cocaine by its inhibition of GAPDH nitrosylation.

Figure 5A:
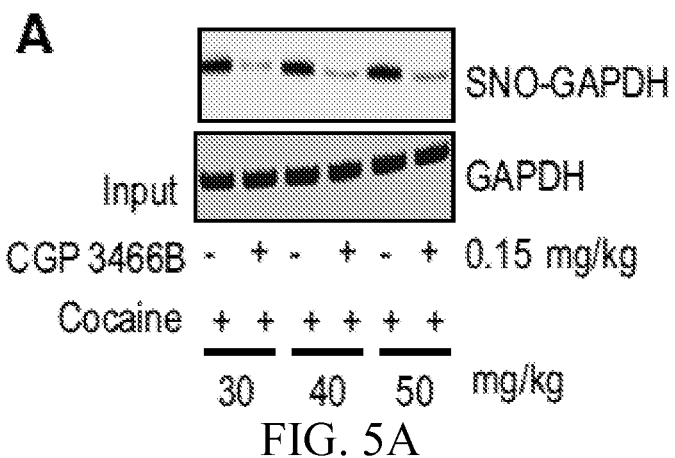
FIGS. 5A and 5B: Nitrosylation levels of GAPDH (FIG. 5A) and nuclear translocation of GAPDH (FIG. 5B) in striatum were decreased in mice treated with cocaine and CGP3466B compared to cocaine treated mice.
Figure 5B:
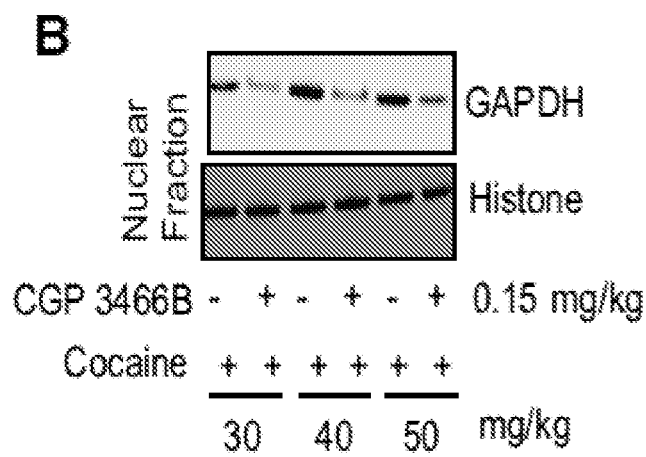

Effects of CGP3466B on Neurotoxic Effects of Cocaine. These experiments establish that the NO-GAPDH signaling pathway mediates behavioral-stimulant effects of cocaine. We wondered whether this cascade also participates in neurotoxic influences of cocaine. Accordingly, we explored actions of higher doses of cocaine (30-50 mg/kg) administered daily for 5 days with or without CGP3466B. These higher doses of cocaine elicit robust nitrosylation of GAPDH in the striatum, effects abolished by CGP3466B (FIG. 5A). Similarly, nuclear translocation of GAPDH at these doses of cocaine is prevented by CGP3466B (FIG. 5B).

Figure 5C:
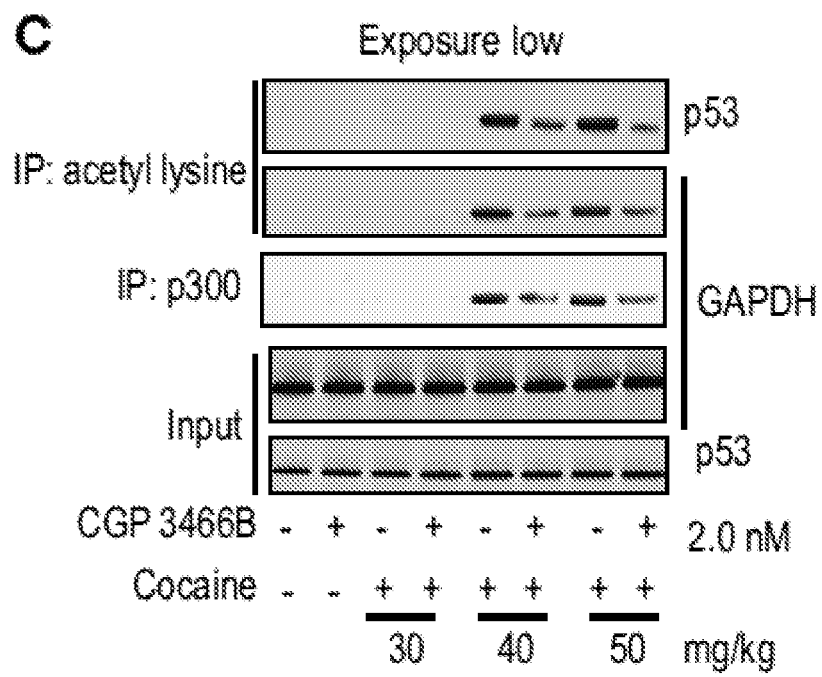
FIG. 5C: Acetylation of GAPDH and p53, as well as p300-GAPDH association in mice treated with cocaine with or without treatment by CGP3466B.
Figure 5D:
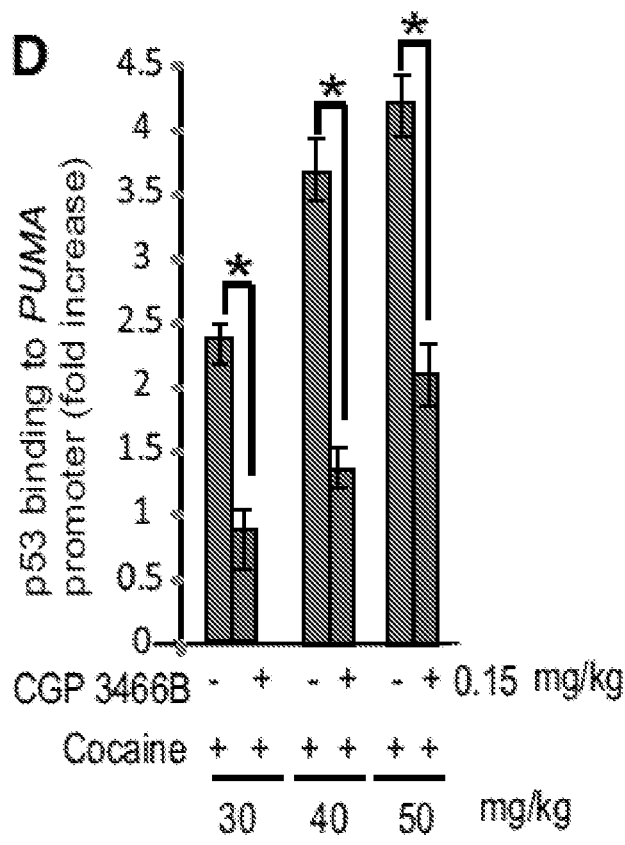
FIGS. 5D and 5E: Analysis of p53 binding to PUMA promoter (FIG. 5D) and c-fos and PUMA levels (FIG. 5E) in mice treated with cocaine with or without CGP3466B. *p<0.01, n=3, one-way ANOVA, mean±SEM.
Figure 5E:
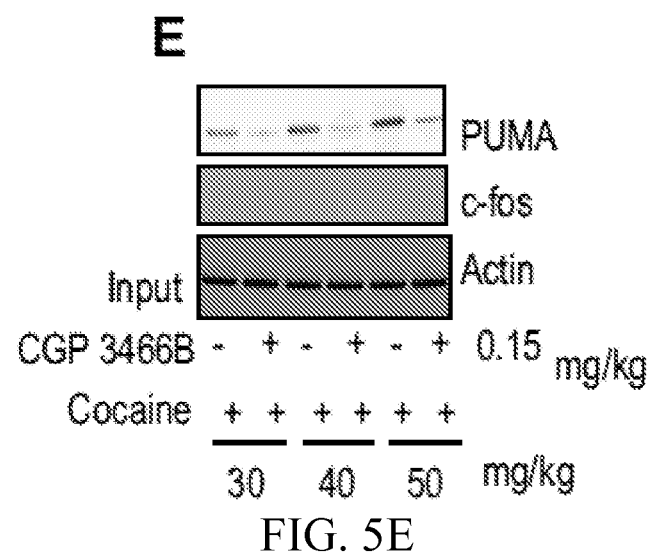

Earlier, we reported that cytotoxic insults, via the NO-GAPDH pathway, lead to binding of GAPDH to the protein acetylating enzyme p300, which in turn acetylates GAPDH and activates the transcriptional activity of p53, resulting in induction of PUMA (Sen et al., 2008). Neurotoxic doses of cocaine augment binding of p300-GAPDH and acetylation of both GAPDH and p53 in the striatum of intact animals (FIG. 5C and S4A). Activation of p53 leads to increases in p53 binding to the PUMA promoter (FIG. 5D) and augmentation of PUMA levels (FIG. 5E). However, in contrast to low doses of cocaine, which activate c-fos but not PUMA, at high cocaine doses c-fos is undetectable, while PUMA expression is increased. CGP3466B blocks activation of p53 (FIGS. 5C and 5D) and induction of PUMA level (FIG. 5E).

Figure 5F:
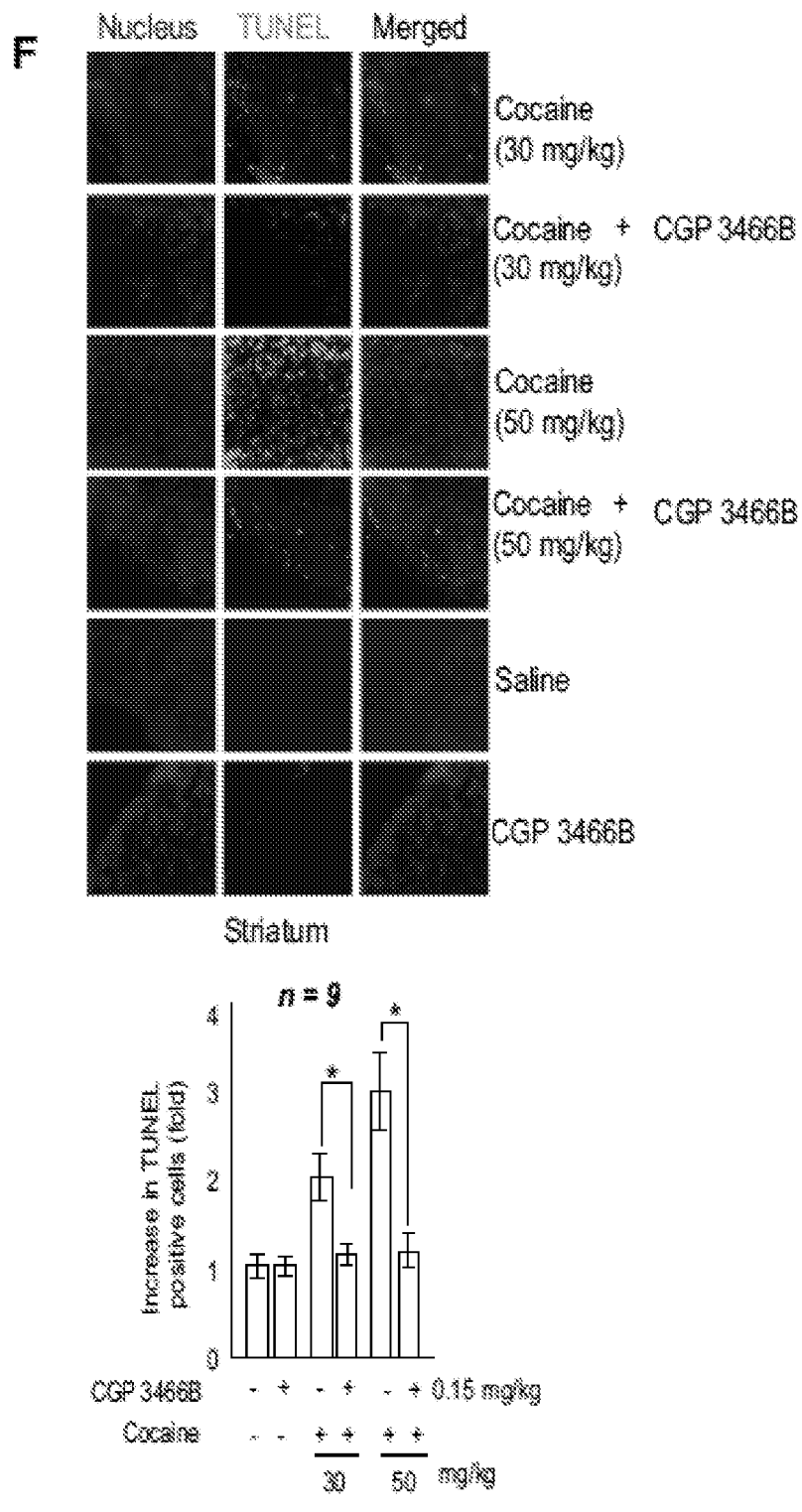
FIG. 5F: Analysis of cell death by TUNEL assay in striatum induced by cocaine with or without chronic treatment with CGP3466B in mice. *p<0.01, n=9, one-way ANOVA, mean±SEM.

To evaluate cocaine neurotoxicity, we monitored apoptosis utilizing the TUNEL procedure (FIG. 5F). Cellular apoptosis is increased by cocaine at 30 mg/kg with substantially greater effects at 50 mg/kg. Treatment with CGP3466B markedly reduces apoptosis.

Figure 5G:
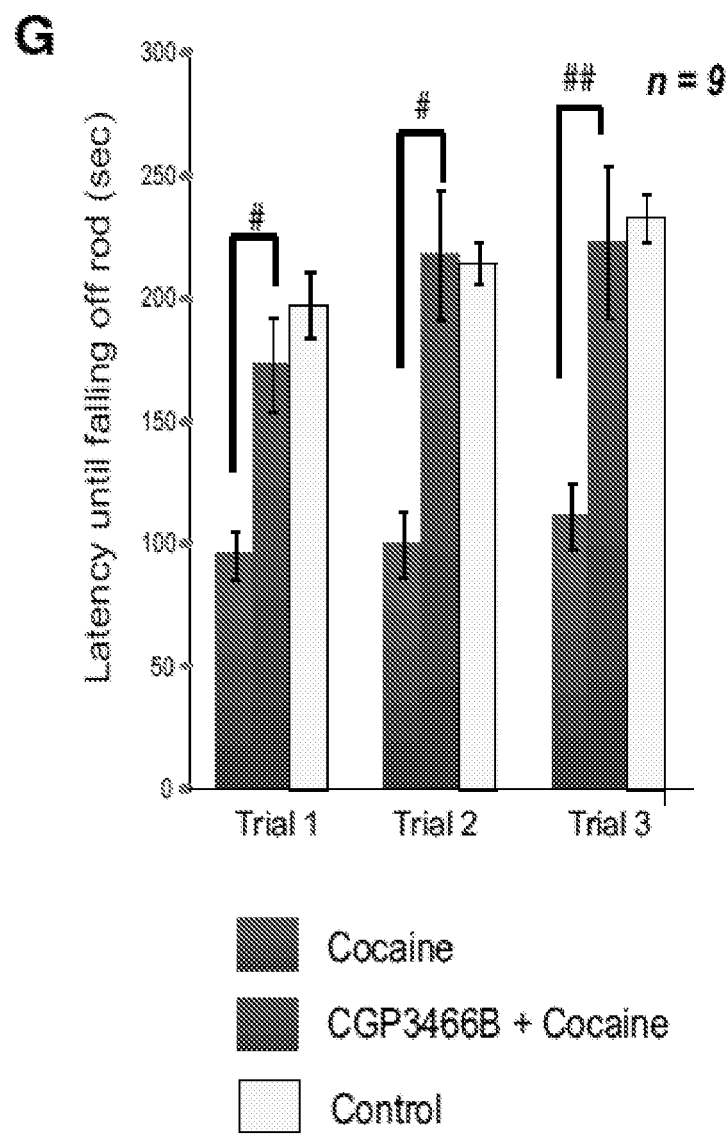
FIG. 5G: Balance and coordination of motor activity evaluated by rotarod analysis test in mice receiving cocaine with or without CGP3466B. #p<0.05, ##p<0.01, n=9, two-way ANOVA, mean±SEM. See also FIG. 9.
Figure 9A:
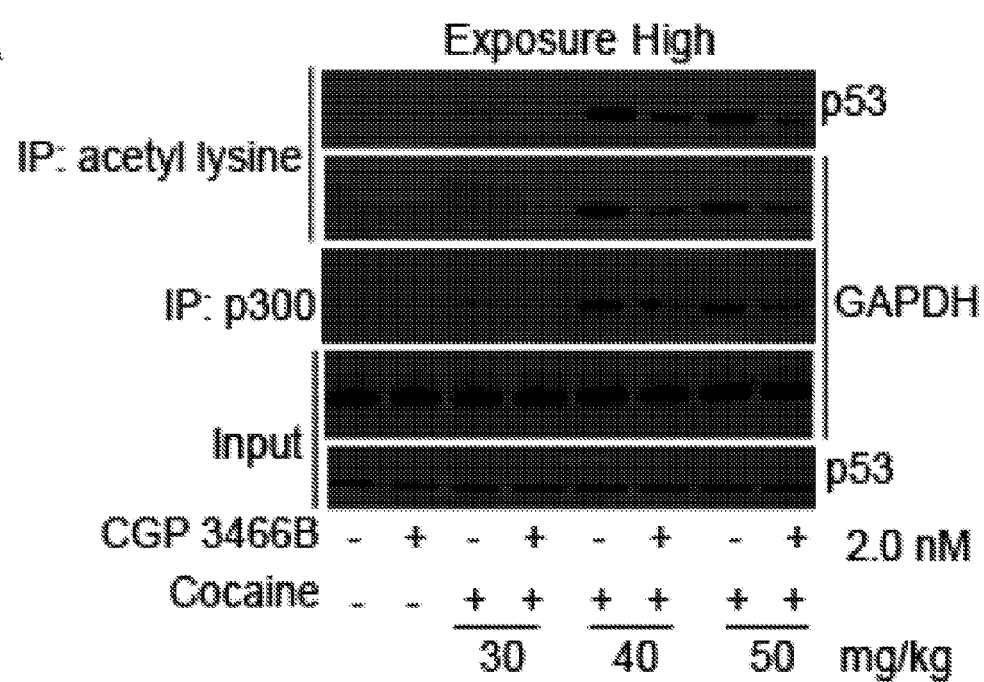
FIG. 9A: Acetylation of both GAPDH and p53 and interaction between p300-GAPDH were monitored through western blot analysis. High exposure blot is shown here.
Figure 9B:
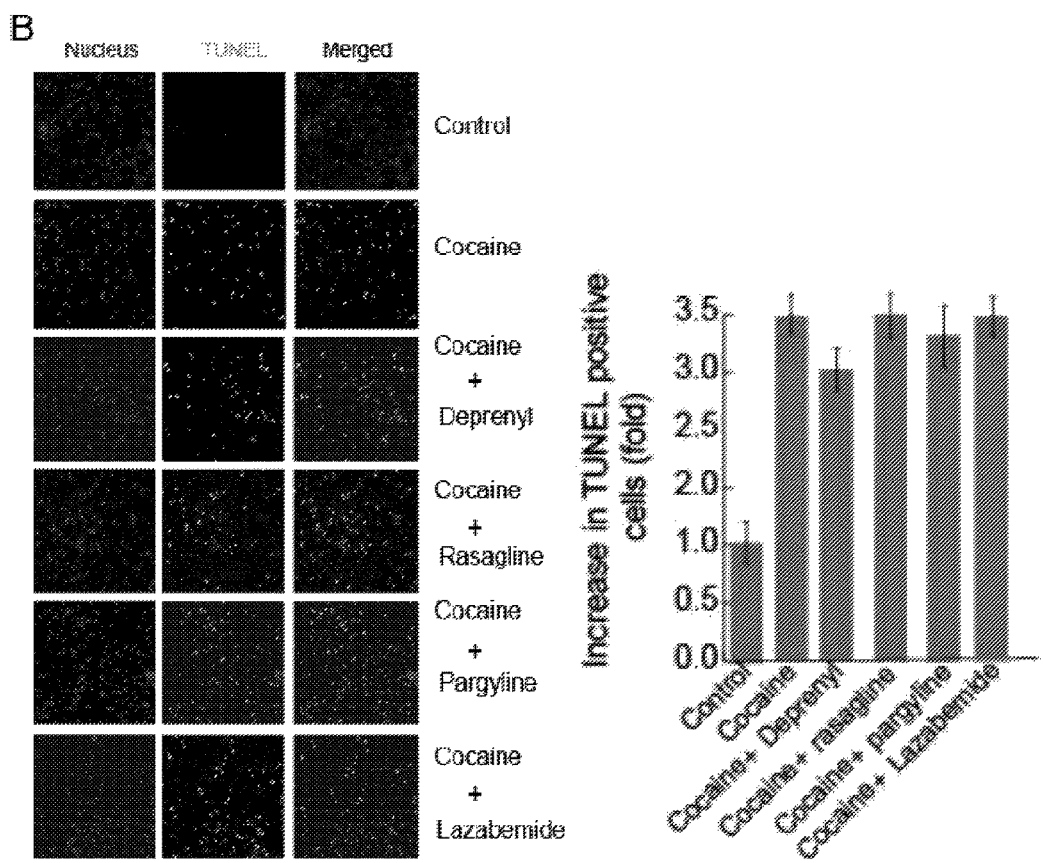
FIG. 9B: Analysis of cell death in striatum of mice treated with cocaine alone or with cocaine along with deprenyl, rasagiline, lazabemide or pargyline.
Figure 9C:
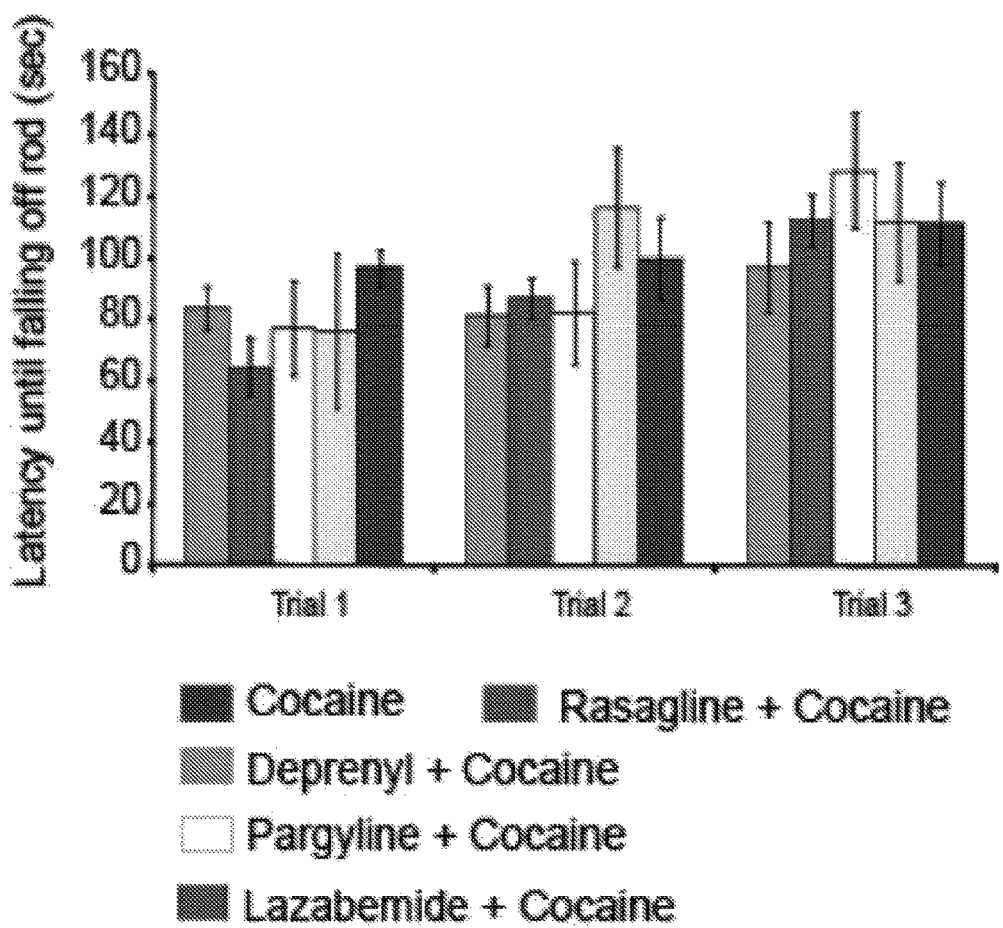
FIG. 9C: Balance and coordination were measured by rotarod analysis following treatment with cocaine alone or with cocaine along with deprenyl, rasagiline, lazabemide or pargyline.

As a behavioral index of neurotoxic insults of cocaine, we examined motor coordination in the rotarod test (FIG. 5G). At 50 mg/kg cocaine disrupts performance, substantially lowering the latency for falling off the rod. Co-treatment with CGP3466B markedly improves performance, increasing latency 2.5- to 3-fold. By contrast, the MAO-B inhibitors deprenyl, rasagiline, pargyline, and lazabemide do not rescue cocaine induced cell death (FIG. 9B) and do not improve rotarod performance (FIG. 9C). Moreover, under basal conditions in the absence of cocaine, these drugs do not affect rotarod performance. The failure of deprenyl to elicit protective effects in these experimental conditions may reflect its monoamine oxidase inhibitory actions potentiating the disruptive influences of cocaine.

Discussion

In summary, our study establishes that cocaine signals by stimulating the NOGAPDH signaling cascade involving nuclear translocation of GAPDH to alter transcriptional events. At lower, behavioral stimulant doses cocaine predominantly signals through CREB, thence the c-fos promoter, activating transcription of genes such as BDNF and Arc. By contrast, high, neurotoxic doses preponderantly elicit p53 mediated transcription of prodeath genes such as PUMA and Bax. Earlier, we differentiated molecular mechanisms for cytotoxic versus neurotrophic signaling by the NO-GAPDH system (Sen et al., 2008; Sen and Snyder, 2011). Following cytotoxic insults nuclear GAPDH activates acetylation by p300/CBP of p53 leading to prodeath gene stimulation (Sen et al., 2008). On the other hand, physiologic stimulation by neurotrophic agents such as BDNF and NGF elicits nuclear association of GAPDH with Siah1 in a complex with the histone methylating enzyme SUV39H1 (Sen and Snyder, 2011). In this complex Siah1, via its ubiquitin E3 ligase activity, elicits degradation of SUV39H1. The resultant decreased methylation of histone H3K9 leads to augmented acetylation of this histone and increased transcription by CREB leading to enhanced neuronal outgrowth (Sen and Snyder, 2011). We presume that the behavioral-stimulant and neurotoxic actions of cocaine reflect the signaling systems linked to CREB and p53, respectively.

We employed CGP3466B as a tool to inhibit GAPDH nitrosylation potently and selectively and thereby disrupt the signaling cascade. CGP3466B prevents transcriptional signaling of cocaine and reverses both the behavioral stimuli and the neurotoxic actions of cocaine. Deprenyl, which like CGP3466B, blocks GAPDH nitrosylation, also reduces behavioral-stimulant effects of cocaine. Its actions contrast with those of other monoamine oxidase inhibitors that do not affect GAPDH nitrosylation and which, instead, augment cocaine's stimulant influences.

Our studies may have therapeutic implications. In this context it is notable that pretreatment with CGP3466B reduces conditioned placed preference, a measure of cocaine seeking behavior. Individuals ingesting high doses of cocaine often experience life-threatening brain damage. The ability of CGP3466B to decrease the neurotoxic effects of cocaine implies that drugs such as CGP3466B may be of value in treating cocaine overdose. CGP3466B and related drugs display neuroprotective actions in numerous animal models including Parkinson's disease (Hara et al., 2006; LeWitt, 2004; Olanow et al., 2006; Waldmeier et al., 2000) motorneuron disease (Sagot et al., 2000), muscular dystrophy (Erb et al., 2009; Meinen et al., 2011), and amyotrophic lateral sclerosis (Leigh et al., 2004; Miller et al., 2007).

We claim:

1. A method of reducing cocaine abuse in a patient in need thereof comprising administering to the patient CGP3446B or Deprenyl for at least one day in the absence of cocaine, wherein the CGP3446B or Deprenyl is administered in an amount sufficient to (1) prevent the nitrosylation of GAPDH by nitric oxide, (2) inhibit the binding of GAPDH to Siah, or (3) prevent the nuclear translocation of GAPDH.

2. The method of claim 1, wherein the compound is CGP3446B.

3. The method of claim 1, wherein the compound is Deprenyl.

* * * * *